US007504507B2

(12) United States Patent
Baguley et al.

(10) Patent No.: US 7,504,507 B2
(45) Date of Patent: Mar. 17, 2009

(54) ANTI-TUMOUR POLYCYCLIC CARBOXAMIDES

(75) Inventors: Bruce Charles Baguley, Auckland (NZ); Leslie William Deady, Heidelberg (AU); William Alexander Denny, Aukland (NZ); Thomas Rodemann, Mount Stuart (AU); Michael Leslie Rogers, Eltham (AU)

(73) Assignee: Auckland Uniservices Limited, Auckland (NZ)

( * ) Notice: Subject to any disclaimer, the term of this patent is extended or adjusted under 35 U.S.C. 154(b) by 538 days.

(21) Appl. No.: 10/514,523

(22) PCT Filed: May 12, 2003

(86) PCT No.: PCT/AU03/00569

§ 371 (c)(1),
(2), (4) Date: May 4, 2005

(87) PCT Pub. No.: WO03/097642

PCT Pub. Date: Nov. 27, 2003

(65) Prior Publication Data

US 2005/0245561 A1 Nov. 3, 2005

(30) Foreign Application Priority Data

May 15, 2002 (AU) .................................. PS2344

(51) Int. Cl.
*C07D 221/06* (2006.01)
*C07D 455/04* (2006.01)
*C07D 471/00* (2006.01)
(52) U.S. Cl. .............................. 546/79; 546/80; 546/81
(58) Field of Classification Search ................ 546/80, 546/79, 81; 514/291
See application file for complete search history.

(56) References Cited

OTHER PUBLICATIONS

Deady et al. Journal of Heterocyclic Chemistry, 38, 1185-, 2001. p. 1186, formula 3c.*
Ames et al., "Condensation of β-Dicarbonyl Compounds with Halogenopyridinecarboxylic Acids. A Convenient Syntehsis of Some Naphthyridine Derivatives," *J. Chem. Soc. Perkin Trans.*, 1:705-710 (1972).
Antonini et al., "Synthesis of (Dialkylamino)alkyl-Disubstituted Pyrimido[5,6,1-*de*]acridines, a Novel Group of Anticancer Agents Active on a Multidrug Resistant Cell Line," *J. Med. Chem.*, 38:3282-3286 (1995).
Asbury et al., "A Phase II Trial of Amonafide in Patients With Endometrial Cancer: A Gynecologic Oncology Group Study," *Am. J. Clin. Oncol.*, 21:406-407 (1998).
Asherson et al., "Synthesis of a Variety of Polycyclic Heteroaromatic Compounds via Quinone Methide Intermediates," *J. Chem. Soc., Chem. Comm.*, 916 (1977).
Atwell, et al., "Potential Antitumor Agents. 50. In Vivo Solid-Tumour Activity of Derivatives of N-[2-(Dimethylamino)ethyl]acridine-4-carboxamine," *J. Med. Chem.*, 30:664-669 (1987).
Baguley et al., Experimental solid tumour activity of *N*-[2-(dimethylamino)ethyl]-acridine-4-carboxamide, *Cancer Chemother. and Pharmacol.*, 36:244-248 (1995).
Cholody et al., "Bisimidazoacridones and Related Compounds: New Antineoplastic Agents with High Selectivity Against Colon Tumors," *J. Med. Chem.*, 38:3043-3052 (1995).
Cholody et al., "Structure-Activity Relationship for Antineoplastic Imidazoacridinones: Synthesis and Antileukemic Activity in Vivo," *J. Med. Chem.*, 39:1028-1032 (1996).
Deady et al., "Synthesis and Antitumor Properties of N-[2-(Dimethylamino)ethyl]carboxamide Derivatives of Fused Tetracyclic Quinolines and Quinoxalines: A New Class of Putative Topoisomerase Inhibitors," *J. Med. Chem.*, 40:2040-2046 (1997).
Deady et al., "Synthesis and Antitumor Activity of Some Indeno[1,2-*b*]quinoline-based bis Carboxamides," *Bioorg. & Med. Chem.*, 8:977-984 (2000).
Deady et al., "The Reaction of Homophthalic Acid and Some Aza Analogues with Vilsmeier Reagent: A Reinvestigation," *J. Heterocycl. Chem.*, 38:1185-1190 (2001).
Denny, W.A., Proceedings of the 13th Annual Conference of the Royal Australian Chemical Institute Medicinal and Agricultural Division 1996, Abstract 5-1.
Diab et al., "A Phase I and Pharmacokinetic Study of Losoxantrone and Paclitaxel in Patients with Advanced Solid Tumors," *Clin. Cancer Res.*, 5:299-308 (1999).
Finlay et al., "Multiple Patterns of Resistance of Human Leukemia Cell Sublines to Amsacrine Analogues," *J. Natl. Cancer Inst.*, 82:622-667 (1990).
Finlay et al., "Comparison of the Effects of Genistein and Amsacrine on Leukemia Cell Proliferation," *Oncol. Res.*, 6:33-37 (1994).
Gabriel et al., "Zur Kenntniss des Benzylidenphtalide (II)," *Ber. Dtsch. Chem. Ges.*, 18:2433-2451 (1885).
Gabriel et al., "Zur Kenntniss des Benzylidenphtalide (II)," *Ber. Dtsch. Chem. Ges.*, 18:3470-3480 (1885).

(Continued)

*Primary Examiner*—D. Margaret Seaman
*Assistant Examiner*—Nizal S Chandrakumar
(74) *Attorney, Agent, or Firm*—Ballard Spahr Andrews & Ingersoll, LLP

(57) ABSTRACT

This invention relates to polycyclic carboxamide compounds of the formula (I) with cytotoxicity, processes for their preparation, pharmaceutical compositions containing them and their use in therapy, particularly I the treatment and/or prophylaxis of cellular proliferative disorders such a cancer.

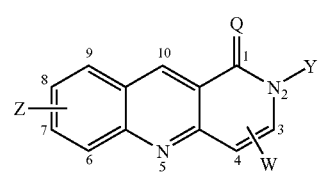

10 Claims, 7 Drawing Sheets

OTHER PUBLICATIONS

Gamage et al., "Dicationic Bis(9-methylphenazine-1-carboxamides): Relationships between Biological Activity and Linker Chain Structure for a Series of Potent Topoisomerase Targeted Anticancer Drugs," *J. Med. Chem.*, 44:1407-1415 (2001).

Goldin et al., "Progress Report on the Screening Program at the Division of Cancer Treatment, National Cancer Institute," *Cancer Treat. Rev.*, 7:167-176 (1980).

Jhalani et al., "Synthesis of 1,6-naphthyridin-5(6*H*)-ones from 8-substituted 7-methylpyrano[4,3-*b*]-pyridine," *Indian J. Chem.*, 28B:173-174 (1989).

Judson, "The Anthrapyrazoles: A New Class of Compounds with Clinical Activity in Breast Cancer," *Semin. Oncol.*, 19(6):687-694 (1992).

Khattab, "Ring Closure of 4-Azido-3-formyl-(or acetyl-)2 pyridones to Isoxazolo[4,3-*c*]pyridones," *Liebigs Ann.*, 393-395 (1996).

Koller et al., "A Phase I-II Trial of Escalating Doses of Mixtoxantrone with Fixed Doses of Cytarabine plus Fludarabine as Salvage Therapy for Patients with Acute Leukemia and the Blastic Phase of Chronic Myelogenous Leukemia," *Cancer*, 86(11):2246-2251 (1999).

Kubo et al. "Synthesis of (3-Carboxy-5-oxo-5*H*-[1]benzopyrano[2,3-*b*]pyridin-2-yl)acetic Acid Derivatives, Potential Antiarthritic Agents," *Chem. Pharm. Bull.*, 34(3):1108-1117 (1986).

Leaf et al., "An ECOG phase II study of Amonafide in Unresectable or Recurrent Carcinoma of the Head and Neck, " *Inv. New Drugs*, 15:165-172 (1997).

Marshall et al., "Microculture-Based Chemosensitivity Testing: A Feasibility Study Comparing Freshly Explanted Human Melanoma Cells with Human Melanoma Cell Lines," *J. Nat. Cancer Inst.*, 84:340-345 (1992).

Marshall et al., "Radiosensitivity of New and Established Human Melanoma Cell Lines: Comparison of [$^3$H]Thymidine Incorporation and Soft Agar Clonogenic Assays," *Eur. J. Cancer*, 30A(9):1370-1376 (1994).

McFadyen, W.D.; Grant, L-C and Denny, W.A., Proceedings of the 13th Annual Conference of the Royal Australian Chemical Institute Medicinal and Agricultural Division 1996, Abstract 5-5.

Meth-Cohn, "Vilsmeier cyclizations in Which the Reagent Nitrogen is Incorporated into the Product: The Actio of *N*-Formyl Derivatives of Cyclic Amines with 2-alkylarylcarboxylic Acids," *Sth. Afr. J. Chem.*, 40:189-190 (1987).

Modi et al., "Isoquinolones: Part IV—Synthesis of 3-Methyl, 3-Formyl & Other 3-Substituted N-Arylisoquinolones," *Indian J. Chem.*, 18B:304-306 (1979).

Riou et al., "Intoplicine (RP 60475) and Its Derivatives, a New Class of Antitumor Agents Inhibiting Both Topoisomerase I and II Activities," *Cancer Res.*, 53:5987-5993 (1993).

Rivalle et al., "Nouvelle Synthèse des pyrido[4,3-*b*]quinoléines substitutés sur leiu sommet 1," *J. Heterocycl. Chem.*, 17:245 (1980).

Sami et al., "2-[2'-(Dimethylamino)ethyl]-1,2-dihydro3*H*-dibenz[*de,h*]isoquinoline-1,3-diones with Substitutents at Positions 4, 8, 9, 10, and 11. Synthesis, Antitumor Activity, and Quantitative Structure-Activity Relationships," *J. Med. Chem.*, 39:4978-4987 (1996).

Skehan et al., "New Colorimetric Cytotoxicity Assay for Anticancer-Drug Screening," *J. Natl. Cancer Inst.*, 82(13):1107-1112 (1990).

Stefanska et al., "6-[(Aminoalkyl)amino]-Substituted 7*H*-Benzo[*e*]perimidin-7-ones as Novel Antineoplastic Agents. Synthesis and Biological Evaluation," *J. Med. Chem.*, 36: 38-41 (1993).

Stewart et al., "Antitumor Activity of XR5944, a Novel and Potent Topoisomerase Poison," *Anticancer Drugs*, 12:359-367 (2001).

Thompson et al., "Phase I Study of DMP 840 in Pediatric Patients with Refractory Solid Tumors," *Inv. New Drugs*, 16:45-49 (1998).

Utsugi et al., "Antitumor activity of TAS-103, a Novel Topoisomerase I and II Inhibitor," *Proc. Am. Assoc. Cancer Res.*, 37:427, Abstract 2915 (1996).

Vicker et al., "Novel Angular Benzophenazines: Dual Topoisomerase I and Topoisomerase II Inhibitors as Potential Anticancer Agents," *J. Med. Chem.*, 45:721-729 (2002).

Vijayalakshmi et al., "Syntehsis of Dibenzol[*b,h*][1,6]naphthyridin-6(5H)-ones," *Indian J. Chem.*, 33B:159 (1994).

Deady L W et al.: "The reaction of homophthalic acid and some aza analogues with Vilsmeier reagent: a reinvestigation", Journal of Heterocyclic Chemistry (2001), 38(5), 1185-1190. (& Chemical Abstracts abstract 136:183737).

Chemical Abstracts abstract 108:94359; Meth-Cohn O: "A versatile synthesis of quinolines and related fused pyridines. 13. Vilsmeier cyclizations in which the reagent nitrogen is incorporated into the product: the action of N-formyl derivatives of cyclic amines with 2-alkylarylcaroxylic acids", S. afr. J. Chem. (1987), 40(3), 189-90.

Chemical Abstracts abstract 100:85564; Meth-Cohn O et al.: "Pyridine annelation of o-methylarylcarboxylic acids with Vilsmeier reagents", Tetrahedron Lett. (1983), 24(42), 4607-10.

Chemical Abstracts abstract 117:150852; Matsui T et al.: "Novel 5-HT3 antagonists. Isoquinolinones and 3-aryl-2-pyridones", J. Med. Chem (1992), 35(18), 3307-19.

Chemical Abstracts abstract 99:88085; Croisy-Delcey M et al.: "Aza analogs of lucanthone: synthesis and antitumour and bactericidal properties", J. Med. Chem. (1983), 26(9), 1329-33.

* cited by examiner 16                      17 a Z = H; b Z = 8-Me; c Z = 7-MeO;

d Z = 4-aza; e Z = 8-aza

R = H except e (R = Et)

(i) $POCl_3$/DMF

Scheme 2a

17                      18

(i) Excess $YNH_2$/DMF/20 °C OR 1.1 mol equiv. $YNH_2$/excess $NEt_3$/DMF/20 °C

Scheme 2b

17b           19           18q

(i) ArNH₂/NEt₃/DMF/20°C    (ii) ArNH₂/NEt₃/pyridine/reflux 8 h

Scheme 2c

(i) SOCl₂/reflux OR CDI/dioxan/reflux    (ii) RNH₂/CH₂Cl₂

Scheme 2d

(i) CDI/dioxan/reflux   (ii) Me₂N(CH₂)₂NH₂/CH₂Cl₂   (iii) 10%NaOH/EtOH/reflux

Scheme 2e (i) CDI/dioxan/reflux   (ii) Me₂N(CH₂)₂NH₂/CH₂Cl₂   (iii) 10%NaOH/EtOH/reflux Scheme 2f

ANTI-TUMOUR POLYCYCLIC CARBOXAMIDES

CROSS REFERENCE TO RELATED APPLICATIONS

The present application claims priority to and the benefit of the filing date of Australian Application No. PS 2344, filed May 15, 2002, which application is incorporated herein fully by this reference.

This invention relates to a novel class of polycyclic carboxamide compounds with cytotoxicity, processes for their preparation, pharmaceutical compositions containing them and their use in therapy, particularly in the treatment and/or prophylaxis of cellular proliferative disorders such as cancer.

BACKGROUND OF THE INVENTION

Compounds comprising polycyclic chromophores bearing a flexible cationic side chain have been known to show cytotoxic effects and to possess utility as anticancer drugs.

Tricyclic chromophores that show cytotoxic activity include benzoisoquinolinediones (e.g., amonafide, 1; Asbury et al., 1998; Leaf et al., 1997), acridine-4-carboxamides (e.g., DACA, 2; Atwell et al., 1987; Baguley et al., 1995; U.S. Pat. No. 4,590,277) and anthraquinones (e.g., mitoxantrone, 3; Koller et al., 1999).

Tetracyclic chromophores with cytotoxic activity include anthrapyrazoles (e.g., losoxantrone, 4; Diab et al., 1999; Judson, 1992), indeno[2,1-c]quinolin-7-ones (e.g., TAS-103, 5; Utsugi et al., 1996), benzophenazines (e.g., XR-11576, 6; Vicker et al., 2002), azonafides (e.g. 7; Sami et al., 1996), imidazoacridinones (e.g. 8; Cholody et al., 1996), pyrimido[5,6,1-de]acridines (e.g. 9; Antonini et al., 1995), benzo[e]pyrido[4,3-b]indoles (e.g., intoplicine, 10; Riou et al., 1993), indeno[1,2-b]quinolines (e.g. 11, Deady et al., 1997) and benzo[e]perimidines (e.g. 12, Stefanska et al., 1993).

Many compounds where two such chromophores are linked by a flexible chain are also effective cytotoxins and anticancer drugs. For example, the bis(naphthalimide) DMP840, 13, was evaluated clinically (Thompson et al., 1998), bis(imidazoacridones) (e.g., WMC-26, 14; Cholody et al. 1995) and bis(phenazines) (e.g., XR5944, 15; Gamage et al., 2001; Stewart et al., 2001) are being considered for clinical trial.

From the publications referred to above, it can be seen that these compounds have a wide variety of different structures. They are considered to be active as anticancer drugs primarily through their ability to inhibit topoisomerase enzymes. However, the relationships between structure, the ability to inhibit topoisomerase enzymes and their potential utility as in vivo anticancer drugs are still not sufficiently well-defined to enable predictions to be made about activity. In view of the potential utility of such compounds, further classes of these compounds are needed.

The present invention relates to amide- (and thioamide) derivatives of benzo[b][1,6]naphthyridin-1 (2H)-one, their synthesis, and their use in the treatment of cancers. The benzo[b][1,6]naphthyridin-1 (2H)-one chromophore (Deady and Rodemann, 2001) and the N2- and carbon-substituted analogues (Asherson and Young, 1977; Khattab, 1996; Meth-Cohn, 1987; Rivalle and Bisagni, 1980) are known including the 6-methyl-1-oxo-1,2-dihydrobenzo[b][1,6]naphthyridine-4-carboxylic acid (Deady and Rodemann, 2001). Dibenzo[b,h][1,6]naphthyridin-6 (5H)-ones have also been reported (Asherson and Young, 1977; Vijayalakshmi and Rajendran, 1994). However, these reports concern the synthesis of the compounds only.

It will be clearly understood that, although a number of prior art publications are referred to herein, this reference does not constitute an admission that any of these documents forms part of the common general knowledge in the art, in Australia or in any other country.

We have now synthesised and evaluated a novel series of carboxamide linked compounds based on benzo[b][1,6]naphthyridin-1 (2H)-one, which differ from previous acridine based compounds by the incorporation of a lactam or thiolactam function in one of the outer rings.

Representative examples of these compounds have utility as cytotoxic and anti-cancer agents.

SUMMARY OF THE INVENTION

According to a first aspect, the invention provides a compound of the formula I

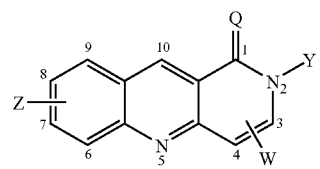

in which positional numbering, where mentioned, refers to the system illustrated above, and one or more W and one or more Z are attached to a ring carbon or carbons at any of positions 3, 4 and 6 to 10, and in which:

Q is O or S;

W is $C(=Q)NR-M-(CH_2)_m R^1$, in which

M is CHJ or G,

R is H or an optionally substituted $C_{1-4}$ alkyl group,

J is H or an optionally substituted $C_1-C_6$ alkyl group,

G is an optionally substituted fully saturated, or partially unsaturated, or aromatic, carbocycle or heterocycle, $R^1$ is $C(=NR^2)NH_2$, $NHC(=NR^3)NH_2$ or $NR^4R^5$, in which each of $R^2$ and $R^3$ are independently H or an optionally substituted $C_{1-4}$ alkyl group, $R^4$ and $R^5$ are independently H or an optionally substituted $C_{1-4}$ alkyl group or $R^4$ and $R^5$ together with the nitrogen atom to which they are attached form an optionally substituted, saturated or unsaturated heterocyclic group, and m is an integer from 0 to 6;

Y is H, $C_{1-6}$ alkyl or $(CH_2)_n-X-(CH_2)_p U$, in which

X is $CH_2$, $C=O$, $CH=CH$, O, S, NR or G; and n and p are integers from 0 to 6, and U is H, $CF_3$, halo, $NR^4R^5$, $^+NRR^4R^5$, cyano, $C(=O)NR^4R^5$ $OR^4$, $CO_2R^4$, G, $NR^4G$ or OG; and Z is H, halo, OH, $CO_2H$, $CO_2R^4$, $SO_2R^4$, $NR^4R^5$, nitro, cyano, $C_{1-6}$ alkyl, $C_{1-6}$ haloalkyl, $C_{1-6}$ alkoxy, $C_{1-6}$ haloalkoxy, $C_{1-6}$ aminoalkyl, $C_{1-6}$ aminoalkoxy, or aza functionality replacing a ring CH functionality, or a carbon or carbon/nitrogen framework bridging the 6-7,7-8 or 8-9 positions so as to form an additional fused 5 to 6-membered carbocycle or heterocycle; or a pharmaceutically-acceptable salt, N-oxide, hydrate, solvate, pharmaceutically acceptable derivative, pro-drug, tautomer and/or isomer thereof.

The optional substituents for R, $R^2$, $R^3$, $R^4$ and $R^5$ are preferably one or more OH or $NH_2$ groups and for J are one or more OH, OMe, $NH_2$, NHMe or $NMe_2$ groups. The preferred optional substituents for G are one or more halo, OH, $CO_2H$, $NR^4R^5$, $NRSO_2R$, $SO_2NR^4R^5$, nitro, cyano, $C_{1-6}$ alkyl, $C_{1-6}$ haloalkyl, $C_{1-6}$ alkoxy, $C_{1-6}$ haloalkoxy, $C_{1-6}$ aminoalkyl, $C_{1-6}$ aminoalkoxy or $B(OR^6)(OR^7)$ in which $R^6$ and $R^7$ are independently hydrogen or an optionally substituted $C_{1-4}$ alkyl group or together with the O and B atoms to which they are attached form an optionally substituted, fully saturated, or partially unsaturated, heterocycle.

Preferably Q is O; W is $CONH(CH_2)_2N(CH_3)_2$ or $CONHCH(CH_3)CH_2N(CH_3)_2$; Y is methyl, butyl or methoxy-substituted phenyl; Z is H, Cl, methyl or methoxy.

A particularly preferred compound is N-[2-(dimethylamino)ethyl]-2,6-dimethyl-1-oxo-1,2-dihydrobenzo[b][1,6]naphthyridine-4-carboxamide or a pharmaceutically acceptable salt or N-oxide thereof.

The present invention also provides a compound of the formula II or III

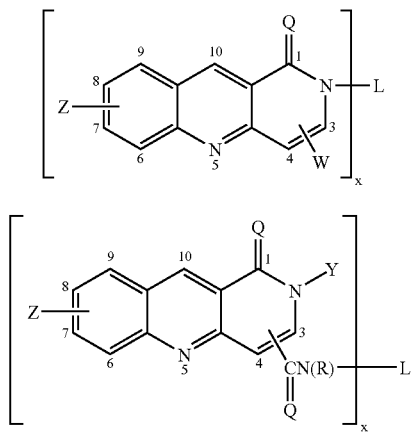

in which one or more W and one or more Z in formula II, and one or more Z and C(=Q)NR in formula III are attached to a ring carbon or carbons at any of positions 3, 4 and 6 to 10 and in which:

Q, R, W, Y and Z are as defined in formula I;

x is an integer from 2 to 4; and

L is a linker group of valency x; or a pharmaceutically-acceptable salt, N-oxide, hydrate, solvate, pharmaceutically acceptable derivative, pro-drug, tautomer and/or isomer thereof.

For the avoidance of any doubt, it is to be understood that each monomer subunit of the compound may be different, provided that in each subunit the substituents are individually within the definitions provided. In other words, compounds with two or more different units of formula I linked together are to be considered to be within the definition of formula II above.

Preferably x is 2.

Preferably L is a nitrogen-containing linker group, more preferably $V^1$-$[(CHR)_q NR^4]_r (CHR)_q$—$V^2$ in which $V^1$ and $V^2$ are each independently oxygen, $NR^4$ or CHR;

q is an integer from 0 to 5 and may have a different value for each subunit of the linker L;

r is an integer from 0 to 2;

$R^4$ is as defined in formula I, or when r is greater than 0, R and $R^4$ may together form an optionally substituted branched or straight chained alkylene.

Preferably R and $R^4$ are each independently H, $CH_3$, or $C_2H_5$, or if r is greater than 0, R and $R^4$ are preferably —$CH_2CH_2CH_2$—.

Most preferably the linker group will be selected from the following:

—$(CH_2)_2NH(CH_2)_2$—
—$(CH_2)_3$—NMe-$(CH_2)_3$—
—$(CH_2)_2NH(CH_2)_2NH(CH_2)_2$—
—$(CH_2)_2NH(CH_2)_3NH(CH_2)_2$—
—$(CH_2)_2NMe(CH_2)_2NMe(CH_2)_2$—
—$(CH_2)_2NMe(CH_2)_3NMe(CH_2)_2$—
—N,N'-Bis(ethylene)piperazine—
—N,N'-Bis(propylene)piperazine-,
—$(CH_2)_s NH(CH_2)_t$—
—$(CH_2)_s NAlkyl(CH_2)_t$—
—$(CH_2)_s NH(CH_2)_t NH(CH_2)_u$—, and
—$(CH_2)_s NAlkyl(CH_2)_t NAlkyl(CH_2)_u$—, in which s, t and u are integers from 2 to 6.

According to a second aspect, the invention provides a process for the preparation of a compound of formula I, II or III which comprises converting a compound of formula IV

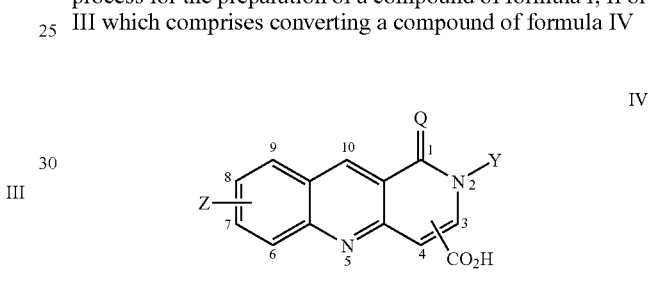

in which one or more Z and one or more $CO_2H$ groups are attached to a ring carbon or carbons at any of positions 3, 4 and 6 to 10; and Q, Y and Z are as defined in formula I into the amide of formula I, II or III.

As the intermediate compound of formula IV is novel, the present invention also extends to compounds of formula IV as defined above.

According to a third aspect, the invention provides a process for the preparation of a compound of formula IV in which Q is O and $CO_2H$ is attached to position 4 comprising reacting a compound of formula V,

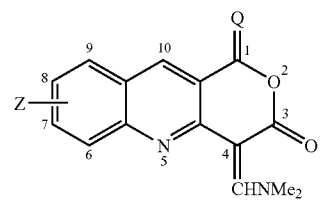

in which Z is as defined in formula I, with $YNH_2$ in which Y is as defined in formula I.

In a fourth aspect, the invention provides a pharmaceutical or veterinary composition comprising the compound of formula I, II or III as defined above, together with a pharmaceutically or veterinarily acceptable carrier.

In a fifth aspect, the invention provides a method of treatment and/or prophylaxis of a cellular proliferative disorder comprising administering a therapeutically effective amount of the compound of formula I, II or III to a subject in need thereof.

The present invention also provides use of the compound of formula I, II or III in the manufacture of a medicament for the treatment and/or prophylaxis of a cellular proliferative disorder.

The present invention further provides the compound of formula I, II or III for use in the treatment and/or prophylaxis of a cellular proliferative disorder.

The present invention still further provides use of a compound of formula I, II or III as a cytotoxic, anti-neoplastic, anti-tumour and/or anti-cancer agent.

DETAILED DESCRIPTION OF THE INVENTION

For the purposes of this specification it will be clearly understood that the word "comprising" means "including but not limited to", and that the word "comprises" has a corresponding meaning.

It must be noted that, as used in the subject specification, the singular forms "a", "an" and "the" include plural aspects unless the context clearly dictates otherwise. Thus, for example, reference to "a compound of formula I, II or III" includes a single compound, as well as two or more compounds; and so forth.

The terms "$C_{1-4}$ alkyl" or "$C_{1-6}$ alkyl" used either alone or in compound words such as "optionally substituted $C_{1-4}$ or $C_{1-6}$ alkyl", "$C_{1-6}$ haloalkyl" or "$C_{1-6}$ aminoalkyl" refer to straight chain, branched chain or cyclic hydrocarbon groups having from 1 to 6 carbon atoms. Illustrative of such alkyl groups are methyl, ethyl, propyl, isopropyl, butyl, isobutyl, sec-butyl, tert-butyl, pentyl, neopentyl, hexyl, cyclopropyl, cyclobutyl, cyclopentyl or cyclohexyl.

The term "heterocyclic group" used either alone or in compound words such as "optionally substituted saturated or unsaturated heterocyclic group" refers to monocyclic or polycyclic heterocyclic groups containing at least one heteroatom atom selected from nitrogen, sulphur and oxygen.

Suitable heterocyclic groups include N-containing heterocyclic groups, such as, unsaturated 3 to 6-membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl;

saturated 3 to 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 3 to 6-membered heteromonocyclic group containing an oxygen atom, such as, pyranyl or furyl;

unsaturated 3 to 6-membered heteromonocyclic group containing 1 to 2 sulphur atoms, such as, thienyl;

unsaturated 3 to 6-membered heteromonocyclic group containing 1 to 2 oxygen atoms and 1 to 3 nitrogen atoms, such as, oxazolyl, isoxazolyl or oxadiazolyl;

saturated 3 to 6-membered heteromonocyclic group containing 1 to 2 oxygen atoms and 1 to 3 nitrogen atoms, such as, morpholinyl;

unsaturated condensed heterocyclic group containing 1 to 2 oxygen atoms and 1 to 3 nitrogen atoms, such as, benzoxazolyl or benzoxadiazolyl;

unsaturated 3 to 6-membered heteromonocyclic group containing 1 to 2 sulphur atoms and 1 to 3 nitrogen atoms, such as, thiazolyl or thiadiazolyl;

saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl.

The term "optionally substituted" refers to a group may or may not be further substituted with one or more groups selected from alkyl, alkenyl, alkynyl, aryl, halo, haloalkyl, haloalkenyl, haloalkynyl, haloaryl, hydroxy; alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy, mercapto, alkylthio, benzylthio, acylthio, phosphorus-containing groups and the like. In some instances in this specification, where substituents may be present, preferred substituents have been mentioned.

The term "carbocycle" refers to a fully saturated, partially unsaturated or aromatic carbocyclic radical having 3 to 12 carbon atoms in a single ring or multiple condensed rings such as cycloalkyl, cycloalkenyl and aryl. Examples of cycloalkyl include cyclopropyl, cyclobutyl, cyclopentyl and cyclohexyl. Examples of cycloalkenyl include cyclobutenyl, cyclopentenyl, cyclopentadienyl and cyclohexenyl. Examples of aryl include phenyl, naphthyl, tetrahydronaphthyl, indane and biphenyl.

The term "halo" or "halogen" refers to fluorine, chlorine, bromine, or iodine. Where halogen substitution is present, preferred halogens are chlorine or bromine.

The term "$C_{1-6}$ alkoxy" used either alone or in compound words such as "$C_{1-6}$ haloalkoxy" or "$C_{1-6}$ aminoalkoxy" refers to straight chain or branched oxy-containing radicals each having alkyl portions of 1 to about 6 carbon atoms. Examples of alkoxy include methoxy, ethoxy, propoxy, butoxy and tert-butoxy.

The term "linker group" is used herein in its broadest sense to refer to any organic group that links together the adjacent units of the compound together and may be symmetrical or non-symmetrical. While the linker group is preferably a nitrogen-containing linker group, it will be appreciated that it could alternatively be O; S; an optionally substituted $C_{1-20}$ alkylene, alkenylene or alkynylene chain which may optionally be interspersed with one or more optionally substituted aryl or optionally substituted heterocyclic groups and/or one or more O, S or N atoms; or an optionally substituted saturated or unsaturated aryl or heterocyclic group.

The terms "alkylene", "alkenylene" and "alkynylene" are the divalent radical equivalents of the terms "alkyl", "alkenyl" and "alkynyl", respectively. The two bonds connecting the alkylene, alkenylene or alkynylene to the adjacent groups may come from the same carbon atom or different carbon atoms in the divalent radical.

The linker may alternatively be of the type disclosed in International Patent Application No. WO 96/25400 by The Du Pont Merck Pharmaceutical Company, the entire disclosure of which is incorporated by this cross-reference.

The term "alkenyl" refers to linear or branched radicals having at least carbon-carbon double bond of 2 to 20 carbon atoms or, preferably 2 to 12 carbon atoms. More preferred alkenyl radicals are "$C_{2-6}$ alkenyl". Examples of alkenyl include ethenyl, propenyl, allyl, propenyl, butenyl and 4-methylbutenyl.

The term "alkynyl" refers to linear or branched radicals having 2 to 20 carbon atoms, preferably 2 to 12 carbon atoms. More preferred alkynyl radicals are "$C_{2-6}$ alkynyl". Examples of alkynyl include propargyl and butynyl.

The conversion step in the process for the preparation of the compound of formula I, II or III may involve an intermediate step in which the compound of formula IV is converted into an imidazolide and then reacted with the appropriate amine to obtain the target amide of formula I, II or III. Alternatively, the reaction involves converting the carboxylic acid of formula IV into an acid halide, followed by reaction with an amine to obtain the target amide of formula I, II or III. The reagent in this second route is preferably thionyl chloride. It will be clearly understood in the above description that in the case of the bis compounds, two units of the carboxylic acid will be reacted with the appropriate diamine to form the target diamide.

The salts of the compound of Formula I, II or III are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within the scope of the invention.

By "pharmaceutically acceptable derivative" is meant any pharmaceutically acceptable salt, hydrate, ester, amide, active metabolite, analogue, residue or any other compound which is not biologically or otherwise undesirable and induces the desired pharmacological and/or physiological effect.

The term "pro-drug" is used herein in its broadest sense to include those compounds which are converted in vivo to compounds of Formula I, II or III.

The term "tautomer" is used herein in its broadest sense to include compounds of Formula I, II or III which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of Formula I, II or III may have one or more chiral centres, it is capable of existing in enantiomeric forms.

The compositions of the present invention comprise at least one compound of Formula I, II or III together with one or more pharmaceutically acceptable carriers and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

By "cellular proliferative disorder" is meant that a cell or cells demonstrate abnormal growth, typically aberrant growth, leading to a neoplasm, tumour or a cancer.

Cellular proliferative disorders include, for example, cancers of the breast, lung, prostate, kidney, skin, neural, ovary, uterus, liver, pancreas, epithelial, gastric, intestinal, exocrine, endocrine, lymphatic, haematopoietic system or head and neck tissue.

Generally, neoplastic diseases are conditions in which abnormal proliferation of cells results in a mass of tissue called a neoplasm or tumour. Neoplasms have varying degrees of abnormalities in structure and behaviour. Some neoplasms are benign while others are malignant or cancerous. An effective treatment of neoplastic disease would be considered a valuable contribution to the search for cancer preventive or curative procedures. The compounds of the invention are preferably used in the treatment of leukaemias, lymphomas, multiple myeloma, sarcomas, and brain tumours, and for cancers of the lung, breast, ovary, testes, and colon.

The term "subject" as used herein refers to any animal having a disease or condition which requires treatment with a pharmaceutically-active agent. The subject may be a mammal, preferably a human, or may be a non-human primate or non-primates such as used in animal model testing. While it is particularly contemplated that the compounds of the invention are suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, felids, canids, bovids, and ungulates.

Suitable mammals include members of the Orders Primates, Rodentia, Lagomorpha, Cetacea, Carnivora, Perissodactyla and Artiodactyla. Members of the Orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The Order Perissodactyla comprises horses and donkeys, which are both economically important and closely related. Indeed, it is well known that horses and donkeys interbreed.

As used herein, the term "therapeutically effective amount" is meant an amount of a compound of the present invention effective to yield a desired therapeutic response, for example, to prevent or treat a cellular proliferative disorder.

The specific "therapeutically effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The compounds of the present invention may additionally be combined with other medicaments to provide an operative combination. It is intended to include any chemically compatible combination of pharmaceutically-active agents, as long as the combination does not eliminate the activity of the compound of formula I, II or III. It will be appreciated that the compound of the invention and the other medicament may be administered separately, sequentially or simultaneously.

Other medicaments may include, for example, one or more other anti-neoplastic agents encompassing but not limited to anti-mitotic agents such as taxol, anti-metabolites such as 5-fluorouracil, hormonal regulators such as tamoxifen, DNA-reactive agents such as cisplatin, or biological agents such as interleukin-2 (IL-2) or antibodies.

A second DNA-binding anti-cancer therapeutic agent could be used in conjunction with administration of the compound of formula I, II or III in order to reduce toxic side effects or side affects to the recipient of either or both of the compound of formula I, II or III or the other anti-cancer agent.

The term "toxic side effects" or "side effects" means the deleterious, unwanted effects of chemotherapy on the subject's normal, non-diseased tissues and organs. For example, toxic side effects may include bone marrow suppression (including neutropenia), cardiac toxicity, hair loss, gastrointestinal toxicity (including nausea and vomiting), neurotoxicity, lung toxicity and asthma. The aldehyde-releasing compound and/or chemotherapeutic agents may be administered orally, topically, or parenterally in dosage unit formulations containing conventional non-toxic pharmaceutically acceptable carriers, adjuvants, and vehicles.

It is contemplated that compounds of the invention may also be administered in the form of tumour-activated pro-drugs, in which the active agent is linked to a 'trigger' domain; such compounds may for example be designed to be activated by local hypoxia within a tumour mass. Suitable methods are known the in the art; see for example Denny, 1996; McFadyen et al, 1996.

The compound of the invention may also be used in combination with agents which relieve side effects caused by drug treatment such as granulocyte-macrophage-colony stimulating factor (GM-CSF), or anti-emetics.

As used herein, a "pharmaceutical carrier" is a pharmaceutically acceptable solvent, suspending agent or vehicle for delivering the compound of formula I, II or III to the subject. The carrier may be liquid or solid and is selected with the planned manner of administration in mind. Each carrier must be pharmaceutically "acceptable" in the sense of being compatible with other ingredients of the composition and non injurious to the subject.

The compound of formula I, II or III may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques.

The present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The compound of formula I, II or III as well as the pharmaceutically-active agent useful in the method of the invention can be administered, for in vivo application, parenterally by injection or by gradual perfusion over time independently or together. Administration may be intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The invention includes various pharmaceutical compositions useful for ameliorating disease. The pharmaceutical compositions according to one embodiment of the invention are prepared by bringing a compound of formula I, II or III, analogues, derivatives or salts thereof, or combinations of compound of formula I, II or III and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 20th ed., Williams and Wilkins, Pennsylvania, USA and The National Formulary XIV, 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono-or diglycerides. In addition, fatty acids such as oleic acid find use in the preparation of injectables.

Compounds of formula I, II or III may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula I, II or III may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

The term "therapeutically effective amount" means an amount of the compound of formula I, II or III of the present invention effective to yield a desired therapeutic response. A "prophylactically effective amount" has a similar definition.

Dosage levels of the compound of formula I, II or III of the present invention are of the order of about 0.5 mg to about 20 mg per kilogram body weight, with a preferred dosage range between about 0.5 mg to about 10 mg per kilogram body weight per day (from about 0.5 gms to about 3 gms per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5-30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 10-50% of the immediately-preceding maximum.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

Figure 1:
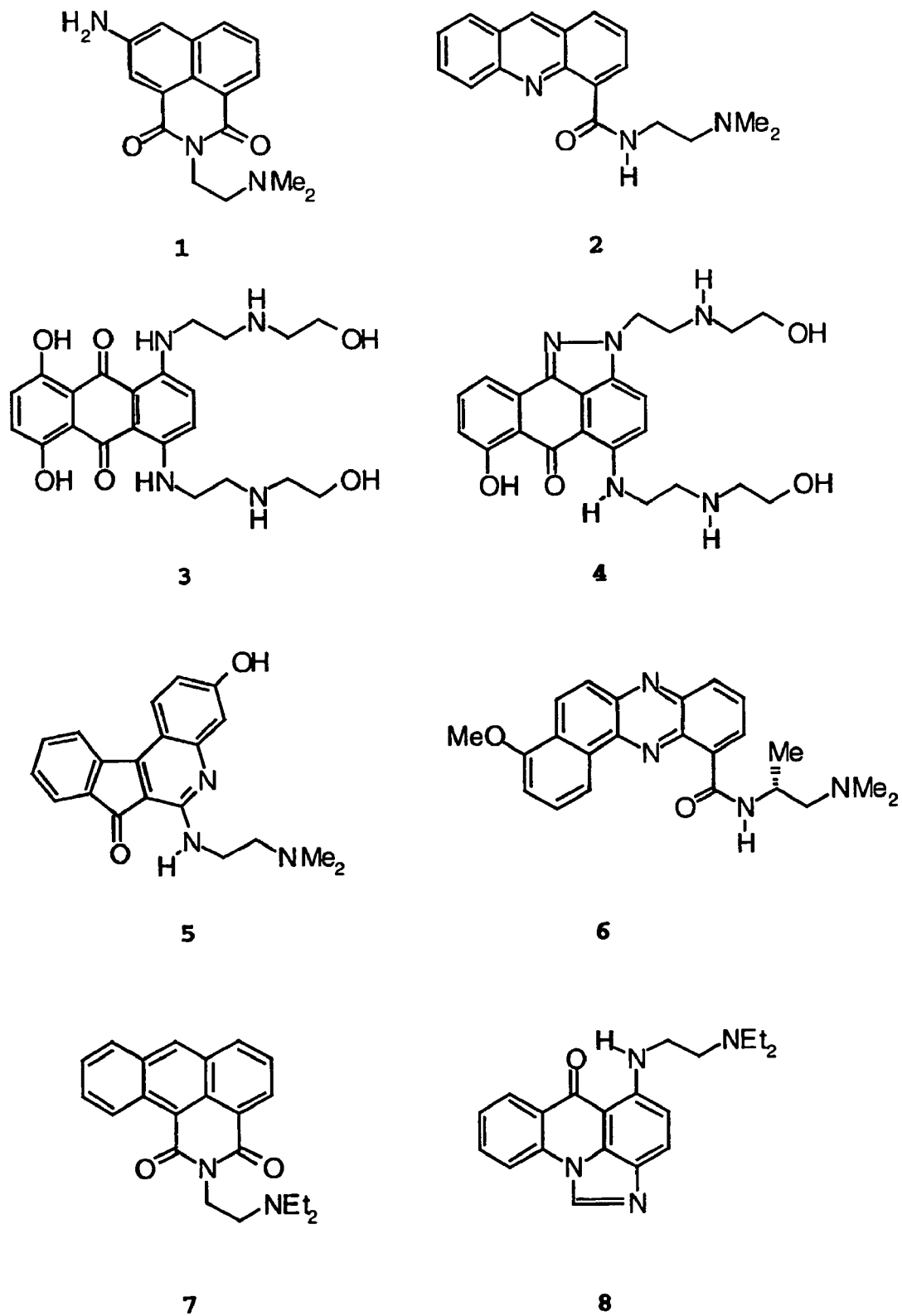
FIG. 1 shows the structures of prior art compounds 1 to 15 referred to herein.
Figure 1:
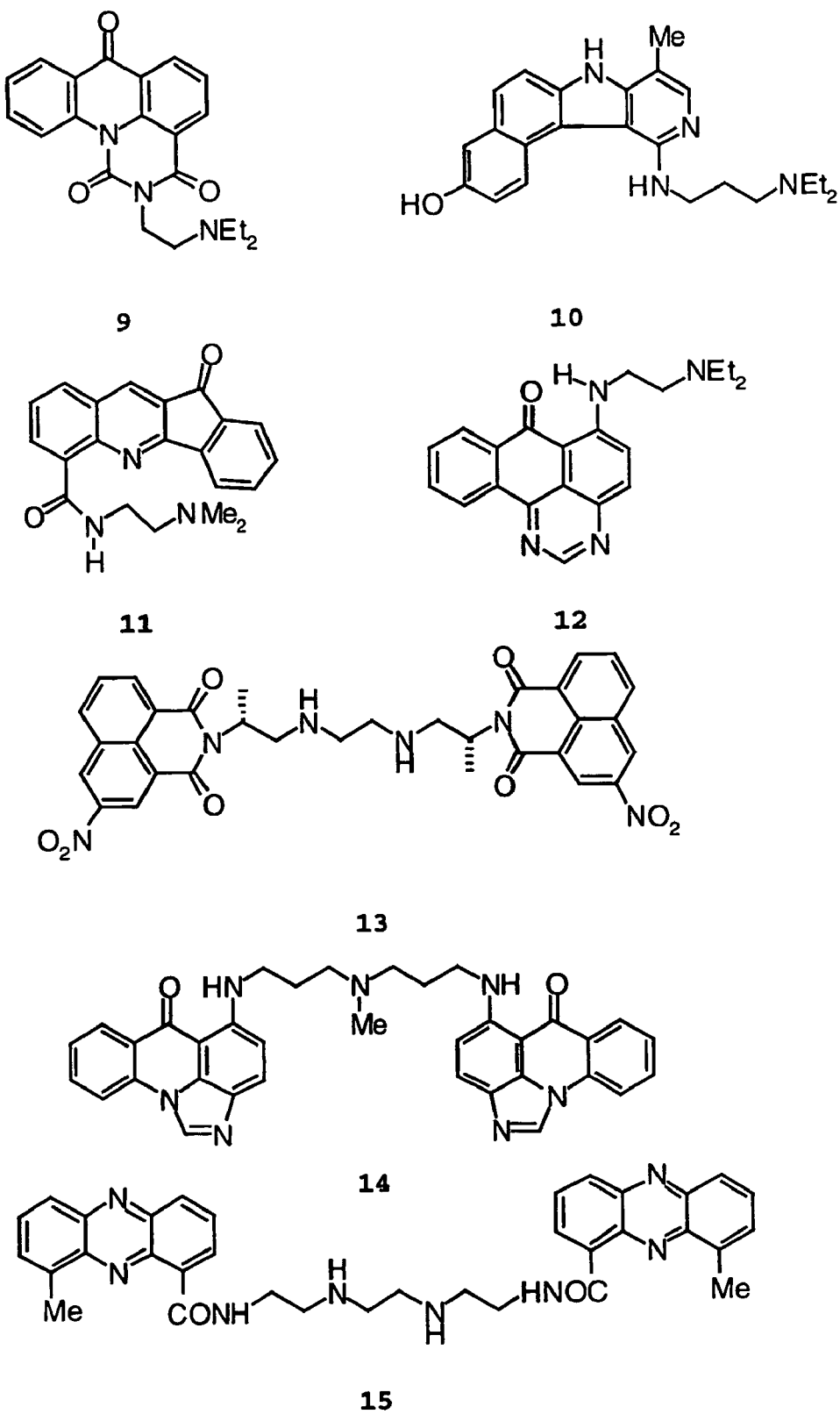
Figure 2:
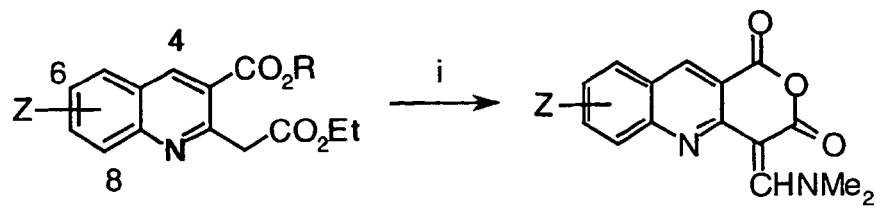
FIG. 2 shows reaction schemes for the preparation of the compounds of Table 1, namely, Scheme 2a—Route to 4H-pyrano[4,3-b]quinoline-1,3-diones; Scheme 2b—Reaction with amines; Scheme 2c—Reaction with 3,4-dimethoxyaniline; Scheme 2d—Preparation of carboxamides; and Schemes 2e and 2f—Preparation of intermediate bis amides and their hydrolysis to mono amides.
Figure 2:
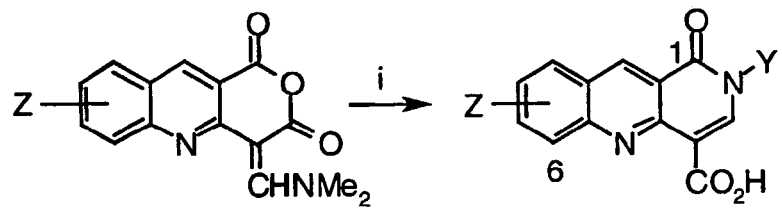
Figure 2:
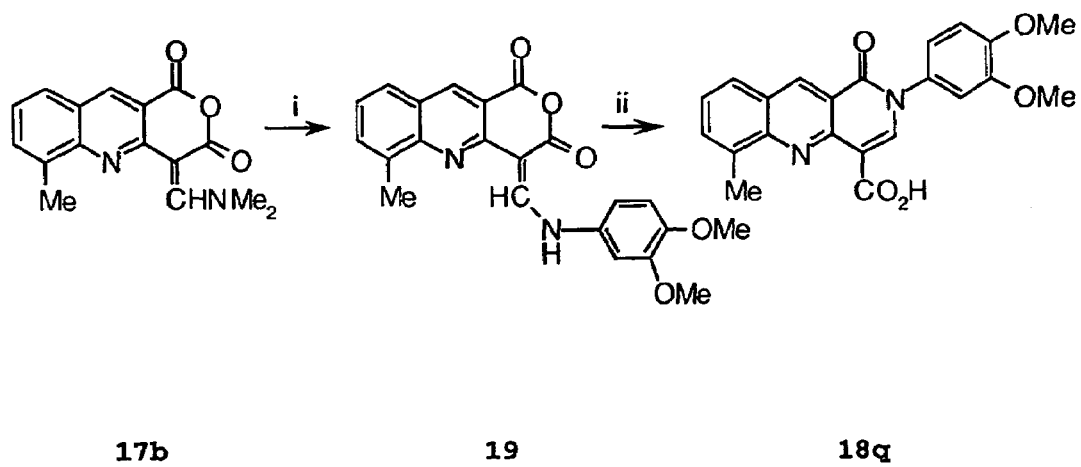
Figure 2:
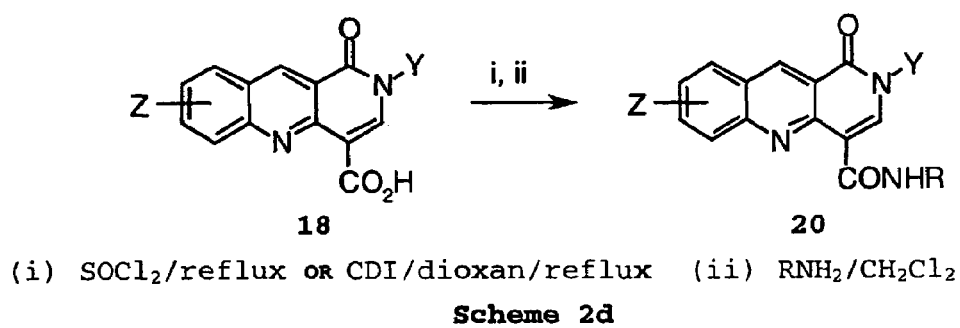
Figure 2:
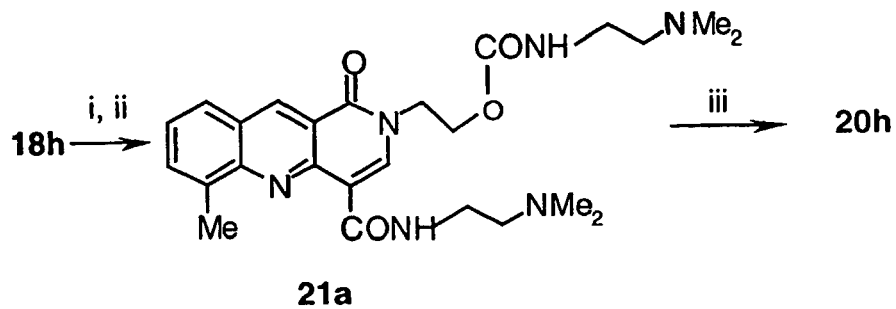
Figure 2:
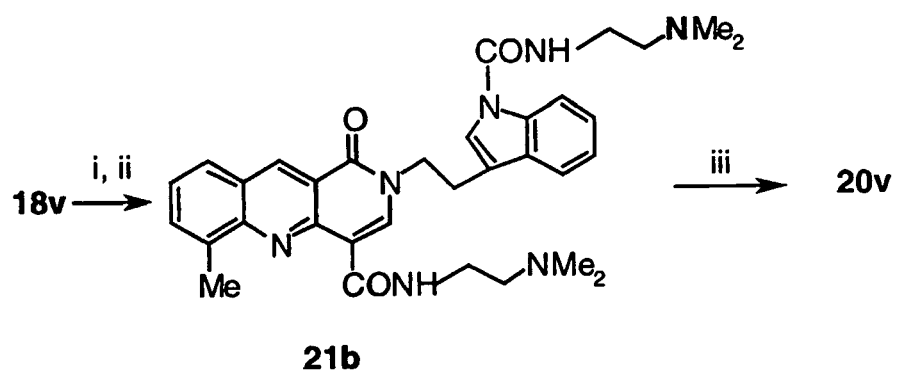

The invention will now be described with reference to the following examples. These examples are not to be construed as limiting the invention in any way.

The structure of representative compounds of the invention is summarised in Table 1. It will be evident that forms A and B represent compounds of general formula I, and II, respectively.

TABLE 1

Representative Compounds of the Invention[a]

| Cpd | Fm | Y | Z |
|---|---|---|---|
| 20b | A | Me | H |
| 20c | A | H | 6-Me |
| 20d | A | Me | 6-Me |
| 20e | A | Et | 6-Me |
| 20f | A | Bu | 6-Me |
| 20g | A | $CH_2CF_3$ | 6-Me |
| 20h | A | $(CH_2)_2OH$ | 6-Me |
| 20i | A | $CH_2CO_2Et$ | 6-Me |
| 20j | A | $(CH_2)_3CO_2Et$ | 6-Me |
| 20k | A | $(CH_2)_2NMe_2$ | 6-Me |
| 20l | A | $(CH_2)_2NMe_2$ | H |
| 20m | A | CH(Me)Ph-(s) | 6-Me |
| 20n | A | Ph | 6-Me |
| 20o | A | $C_6H_4F$-4 | 6-Me |
| 20p | A | $C_6H_4B(OH)_2$-4 | 6-Me |
| 20q | A | $C_6H_3[3,4$-$(MeO)_2]$ | 6-Me |
| 20r | A | $CH_2C_6H_3[3,4$-$(MeO)_2]$ | 6-Me |
| 20s | A | $(CH_2)_2C_6H_3[3,4$-$(MeO)_2]$ | 6-Me |
| 20t | A | $CH_2$(2-pyridinyl) | 6-Me |
| 20u | A | $(CH_2)_3$(N-(2-oxopyrrolidinyl)) | 6-Me |
| 20v | A | $(CH_2)_2$(3-indolyl) | 6-Me |
| 20w | A | Me | 7-MeO |
| 20x | A | Me | 6-Cl-7-MeO |
| 20y | A | Me | 6-aza |
| 20z | A | Me | 10-aza |
| 21a | A | $(CH_2)_2OCONH(CH_2)_2NME_2$ | 6-Me |
| 21b | A | (see structure below) | 6-Me |
| 20aa | B | $(CH_2)_2NMe(CH_2)_3NMe(CH_2)_2$ | 6-Me |
| 20bb | A | Me | 6-Me |
| 20cc | A | Me | 6-Me |

Footnotes

[a] $R = (CH_2)_2NMe_2$ except 20bb [(S)—CH(Me)CONMe$_2$], 20cc [(S)—CH(Me)CH$_2$NMe$_2$]

Chemistry

The homophthalic acid analogues 16a-d were prepared by adapting a method for the pyridine example (Ames and Dodds, 1972). Analogue 16e was prepared by another literature procedure (Kubo et al, 1986). Reaction of 16 with Vilsmeier reagent gave compounds 17 (Scheme 2a) (Deady and Rodemann, 2001). Compound 18d was formed previously by refluxing 17b with phosphoryl chloride for 48 h (Deady and Rodemann, 2001). However, reaction with methylamine in tetrahydrofuran/dimethylformamide at room temperature brought about the same conversion in an experimentally preferable procedure; the other 17 reacted similarly. The related reaction of isocoumarins with ammonia to give isoquinolones [the Gabriel reaction (Gabriel, 1885)] is known and has been extended in related systems to reactions with alkyl (Jhalani et al, 1989) and aryl (Modi and Usgaonkar, 1979) amines. Compounds 17 reacted with a wide selection of amines under very mild conditions, to give 18 (Scheme 2b) in generally good yields, while reaction of 17b with N,N'-bis-(2-aminoethyl)-N,N'-dimethylpropane-1,3-diamine gave an example of a bis compound 18aa.

A slight anomaly occurred when ammonia was used as the alkyl amine, as the product which separated from the reaction mixture was the ammonium salt of the acid; liberation of 18c required treatment with acid.

Reaction of 17 with arylamines failed in the absence of triethylamine, and it seems that moderate base catalysis of this reaction is required. Alkyl amines behave as both nucleophile and base, but arylamines required the presence of the more basic, non-nucleophilic triethylamine. Even so, a complication arose because the dimethylamine liberated during the reaction competed with the arylamine and led to formation of a byproduct. This was minimised by using a large excess of the arylamine. In the case of 3,4-dimethoxyaniline, this complication did not arise because the initial product, 19, was very insoluble. To get the completed reaction, reflux in pyridine for 8 h of a mixture of 19, more 3,4-dimethoxyaniline and triethylamine was required, and gave 18q in 78% yield (Scheme 2c).

The carboxamides of Table 1 were prepared by reaction of the intermediate acid chlorides (from thionyl chloride reaction with 18, and not isolated) or imidazolides (from 1,1'-carbonyldiimidazole reaction with 18, and not isolated) with the appropriate amine.

Experimental

NMR spectra were recorded on a Bruker AM-300 spectrometer operating at 300.13 MHz ($^1$H) and 75.47 MHz ($^{13}$C) and a Bruker DRX-400 spectrometer operating at 400.13 MHz ($^1$H) and 100.62 MHz ($^{13}$C) and chemical shifts are reported as δ values (ppm) relative to Me$_4$Si. COSY spectra were recorded on the AM-300 spectrometer using the pulse program COSY .AUR from the Bruker library. HMQC and HMBC spectra were recorded on the DRX-400 spectrometer using the pulse programs INV4GSTP and INV4GSLPLRND, respectively. NOESY spectra were recorded on the Bruker DRX-400 spectrometer using the pulse program NOESYTP from the Bruker library. Various standard techniques were used to identify proton-bound carbons in $^{13}$C NMR spectra. Electrospray mass spectra (ESMS) were recorded on a VG Bio-Q triple quadrupole Mass Spectrometer using methanol or acetonitrile with formic acid (1%) as mobile phase. EI and LSI (3-nitrobenzyl alcohol as liquid matrix) mode high-resolution mass spectra were obtained by Dr N. Davies, University of Tasmania, Australia. Microanalyses were performed at the Campbell Microanalytical Laboratory, University of Otago, New Zealand.

N,N'-Bis-(2-aminoethyl)-N,N'-dimethylpropane-1,3-diamine was available (Deady et al, 2000) and the other amines were commercial samples.

Precursor compounds 16a-d were prepared by adapting a method for the pyridine analogue (Ames and Dodds, 1972):

Ethyl(3-Carboxyquinolin-2-yl)acetate (16a), obtained as a beige solid, mp 170-171° C. (from acetonitrile). $^1$H NMR (CDCl$_3$): δ 1.24 (t, 3H, J=7.1 Hz), 4.20 (q, 2H, J=7.1 Hz), 4.57 (s, 2H), 7.58 (t, 1H, J=7.6 Hz), 7.82 (t, 1H, J=7.5 Hz), 7.91 (d, 1H, J=8.0 Hz), 8.19 (d, 1H, J=8.5 Hz), 9.00 (s, 1H), 12.28 (br s, 1H).

Ethyl(3-Carboxy-8-methylquinolin-2-yl)acetate (16b), as reported (Deady and Rodemann, 2001)

Ethyl(3-Carboxy-7-methoxyquinolin-2-yl)acetate (16c), obtained as an orange solid, mp 193-195° C. (dec) (from ethanol). Occasionally, the compound was obtained as a red oil, which solidified on trituration with cold acetonitrile. Recrystallization was not necessary prior to use in the next step. $^1$H NMR (CDCl$_3$): δ 1.22 (t, J=7.1 Hz, 3H, CO$_2$CH$_2$CH$_3$), 4.02 (s, 3H, ArOCH$_3$), 4.16 (q, J=7.1 Hz, 2H, CO$_2$CH$_2$CH$_3$), 4.65 (s, 2H, CH$_2$CO$_2$Et), 7.33 (dd, J=9.1, 1.8 Hz, 1H), 7.88 (m, 2H), 9.05 (s, 1H).

Ethyl(3-Carboxyquinoxalin-2-yl)acetate (16d), obtained as a brown semi-solid, which was used in this state in the next step.

Ethyl(3-Ethoxycarbonyl[1,8]naphthyridin-2-yl)acetate (16e) was prepared from 2-aminonicotinaldehyde and diethyl 1,3-acetonedicarboxylate by the method reported for the dimethyl analogue (Kubo et al, 1986), as an orange solid, mp 79-80° C. (from ethyl acetate). $^1$H NMR (CDCl$_3$): δ 1.20 (t, J=7.1 Hz, 3H, 2-CO$_2$CH$_2$CH$_3$), 1.39 (t, J=7.1 Hz, 3H, 3-CO$_2$CH$_2$CH$_3$), 4.13 (q, J=7.1 Hz, 2H, 2-CO$_2$CH$_2$CH$_3$), 4.38 (q, J=7.1 Hz, 2H, 3-CO$_2$CH$_2$CH$_3$), 4.49 (s, 2H, CH$_2$CO$_2$Et), 7.52 (dd, J=8.0, 4.2 Hz, 1H, H-6), 8.27 (d, J=7.9 Hz, 1H, H-5), 8.84 (s, 1H, H-4), 9.15 (d, J=2.4 Hz, 1H, H-7).

Example 1

Preparation of 4-Dimethylaminomethylene-6-methyl-4H-pyrano[4,3-b]quinoline-1,3-dione (17b)

This is an example of the general preparation of the diones of Formula V.

Phosphorus oxychloride (13 mL) was added, with stirring at 0° C., to dimethylformamide (40 mL). After a further 20 min., a solution of ethyl(3-carboxy-8-methylquinolin-2-yl) acetate 16b (10.0 g) in dimethylformamide (10 mL) was added in a single portion and the mixture was stirred at room temperature for a further 2 h. The precipitate was collected by filtration and washed with cold acetone to give the product as an orange solid (10.0 g, 97%), mp >295° C. (decomposed-formed needles above 280° C.). $^1$H NMR (d$_6$-DMSO): δ 2.69 (s, 3H, CH$_3$), 3.30 (s, 3H, N—CH$_3$), 3.59 (s, 3H, N—CH$_3$), 7.36 (t, 1H, J=7.6 Hz, H-3), 7.68 (d, 1H, J=7.0 Hz), 7.89 (d, 1H, J=8.1 Hz), 8.81 (s, 1H), 8.93 (s, 1H).

The following compounds were prepared using a similar procedure:

4-Dimethylaminomethylene-4H-pyrano[4,3-b]quinoline-1,3-dione (17a)

From 16a, and obtained as an orange solid (87%), mp >300° C. $^1$H NMR (d$_6$-DMSO): δ 3.33 (s, 3-H, N—CH$_3$), 3.64 (s, 3-H, N—CH$_3$), 7.55 (t, 1-H, J=7.4 Hz), 7.91 (t, 1-H, J=7.3 Hz), 8.08 (d, 1-H, J=7.9 Hz), 8.15 (d, 1-H, J=7.8 Hz), 8.94 (s, 1-H), 9.13 (s, 1-H).

4-Dimethylaminomethylene-7-methoxy-4H-pyrano[4,3-b]quinoline-1,3-dione (17c)

From 16c, and obtained as a bright yellow solid (95%), mp 273-277° C. (after forming needles >230° C.). $^1$H NMR (d$_6$-DMSO): δ 3.33 (s, 3H, NCH$_3$), 3.62 (s, 3H, NCH$_3$), 3.94 (s, 3H, ArOCH$_3$), 7.18 (dd, J=8.9, 1.7 Hz, 1H), 7.57 (s, 1H), 8.03 (d, J=9.0 Hz, 1H), 8.97 (s, 2H).

4-Dimethylaminomethylene-4H-pyrano[3,4-b]quinoxaline-1,3-dione (17d)

From crude 16d, with a changed ratio of 1 g 16d: 0.8 mL POCl$_3$: 1.6 mL DMF. The reaction mixture was heated, with moisture exclusion, at 75° C. for 16 h, then cooled, diluted with cold dichloromethane, and kept at −18° C. for 1 h. The brick red solid was filtered and washed exhaustively, with thorough stirring, with cold dichloromethane to give the dione (22% from 3-chloroquinoxaline-2-carboxylic acid), mp 133-139° C. $^1$H NMR (d$_6$-DMSO): δ 3.27 (s, 3H, NCH$_3$), 3.57 (s, 3H, NCH$_3$), 7.66 (ddd, J=8.3, 6.6, 1.6 Hz, 1H), 7.81-7.92 (m, 2-H), 8.04 (d, J=7.8 Hz, 1H), 8.66 (s, 1H, =HCNMe$_2$). $^{13}$C NMR (d$_6$-DMSO): δ 45.0 (CH$_3$), 48.3 (CH$_3$), 87.0 (C), 127.2 (CH), 128.3 (CH), 130.3 (CH), 133.3 (C), 133.7 (CH), 139.4 (C), 143.2 (C), 150.3 (C), 157.6 (C), 159.7 (C), 161.1 (CH).

9-Dimethylaminomethylene-9H-pyrano[4,3-b][1,8]naphthyridine-6,8-dione (17e)

From diester 16e, with a changed ratio of 1 g 16e: 0.8 mL POCl$_3$: 1.6 mL DMF. The reaction mixture was heated, with moisture exclusion, at 75° C. for 16 h, then cooled, diluted with cold dichloromethane, and kept on ice for 1 h. The orange solid was filtered and washed exhaustively, with thorough stirring, with cold dichloromethane. The mass of orange dione obtained represented >100% yield. It was used in further reaction in this state within 24 h, since it decomposed on long standing. $^1$H NMR (d$_6$-DMSO): δ 3.33 (s, 3H, NCH$_3$), 3.62 (s, 3H, NCH$_3$), 7.67 (dd, J=7.8, 4.9 Hz, 1H), 8.77 (s, 1H), 8.82 (d, J=8.1 Hz, 1H), 9.07 (d, J=4.9 Hz, 1H), 9.15 (s, 1H).

Example 2

Preparation of 2,6-Dimethyl-1-oxo-1,2-dihydrobenzo[b][1,6]naphthyridine-4-carboxylic acid (18d)

This is an example of the general preparation of the carboxylic acids of Formula IV from precursor compounds of Formula V by reaction with an excess of an amine according to Scheme 2b.

A solution of methylamine in tetrahydrofuran (7.0 ml, 2 M) was added to a suspension of 17b (0.8 g) in dimethylformamide (20 mL) and the whole was stirred for 16 h at room temperature. The solid was collected by filtration and washed with cold acetone to give the product as a bright yellow solid (0.60 g, 79%), mp >300° C. (formed cubic crystals above 290° C.). $^1$H NMR (d$_6$-DMSO): δ 2.75 (S, 3H, CH$_3$), 3.67 (s, 3H, N—CH$_3$), 7.67 (t, 1H, J=7.7 Hz, H-8), 7.95 (d, 1H, J=6.6 Hz), 8.25 (d, 1H, J=8.1 Hz), 8.83 (s, 1-H), 9.52 (s, 1-H), 16.03 (S, 1H, COOH).

Anal. Calc. for C$_{15}$H$_{12}$N$_2$O$_3$.0.2H$_2$O: C, 66.3; H, 4.6; N, 10.3. Found: C, 66.6; H, 4.4; N, 10.4.

The following compounds were made using a similar procedure.

2-Methyl-1-oxo-1,2-dihydrobenzo[b][1,6]naphthyridine-4-carboxylic acid (18b)

From 17a and methylamine, as for 18d, and obtained as a yellow solid (69%), mp >305° C. (formed needles >230° C. $^1$H NMR (d$_6$-DMSO): δ 3.61 (S, 3H, N—CH$_3$), 7.71 (t, 1H, J=7.7 Hz), 8.00 (t, 1H, J=8.2 Hz), 8.16 (d, 1H, J=8.6 Hz), 8.33 (d, 1H, J=8.1 Hz), 8.66 (s, 1-H), 9.46 (s, 1-H), 16.00 (s, 1H, COOH).

2-Butyl-6-methyl-1-oxo-1,2-dihydrobenzo[b][1,6]naphthyridine-4-carboxylic acid (18f)

From 17b and butylamine, as for 18d, and obtained as a bright yellow solid (82%), mp 259° C. $^1$H NMR (CDCl$_3$): δ 0.98 (t, 3H, J=7.2 Hz, (Bu)CH$_3$), 1.42 (sextet, 2H, J=7.6 Hz, (Bu)CH$_2$), 1.81 (quintet, 2H, J=7.7 Hz, (Bu)CH$_2$), 2.83 (S, 3H, C6-CH$_3$), 4.10 (t, 2H, J=7.4 Hz, N—CH$_2$), 7.57 (t, 1H, J=7.7 Hz, H-8), 7.81 (d, 1H, J=7.0 Hz, H-7), 7.93 (d, 1H, J=8.3 Hz, H-9), 8.59 (s, 1H, H-3), 9.35 (s, 1H, H-10), 16.09 (br s, 1H, COOH). $^{13}$C NMR (CDCl$_3$): δ 13.6 (γ-CH$_3$), 18.2 (C6-CH$_3$), 19.9 (β-CH$_2$), 31.3 (α-CH$_2$), 49.8 (N—CH$_2$), 105.2 (C-4), 119.1 (C-10a), 126.4 (C-9a), 127.4 (C-8), 127.6 (C-9), 134.2 (C-7), 134.9 (C-6), 141.3 (C-10), 145.2 (C-3), 146.7 (C-5a), 148.7 (C-4a), 161.8 (C-1), 166.3 (COOH).

2-[(2-Dimethylamino)ethyl]-6-methyl-1-oxo-1,2-dihydrobenzo[b][1,6]naphthyridine-4-carboxylic acid (18k)

From 17b and N,N-dimethylethylenediamine, as for 18d, and obtained as a yellow solid (78%), mp 254-255° C. $^1$H NMR (d$_6$-DMSO): δ 2.21 (s, 6H, N(CH$_3$)$_2$), 2.60 (t, 2H, J=6.0 Hz), 2.73 (s, 3H, CH$_3$), 4.23 (t, 2H, J=6.0 Hz), 7.65 (t, 1H, J=7.6 Hz, H-8), 7.93 (d, 1H, J=6.8 Hz), 8.21 (d, 1H, J=8.3 Hz), 8.74 (s, 1H, H-3), 9.48 (s, 1H, H-10).

2-[(2-Dimethylamino)ethyl]-1-oxo-1,2-dihydrobenzo[b][1,6]naphthyridine-4-carboxylic acid (18l)

From 17a and N,N-dimethylethylenediamine, as for 18d, and obtained as a yellow solid (52%), mp 232-233° C. $^1$H NMR (d$_6$-DMSO): δ 2.20 (s, 6H, N(CH3)$_2$), 2.58 (t, 2H, J=5.9 Hz), 4.22 (t, 2H, J=6.0 Hz), 7.77 (t, 1H, J=7.4 Hz), 8.06 (t, 1H, J=7.6 Hz), 8.23 (d, 1H, J=8.6 Hz), 8.39 (d, 1H, J=8.3 Hz), 8.74 (s, 1H, H-3), 9.54 (s, 1H, H-10).

(S)-6-Methyl-1-oxo-2-(1-phenylethyl)-1,2-dihydrobenzo[b][1,6]naphthyridine-4-carboxylic acid (18m)

From 17b and (S)-(−)-α-methylbenzylamine, as for 18d except that the product remained in the dimethylformamide solution. Water was added to the reaction mixture and the resulting precipitate was collected by filtration and washed with water to give the product as a yellow solid (79%), mp 234-235°C. $^1$H NMR (d$_6$-DMSO): δ 1.84 (d, 3H, J=7.1 Hz, CH—CH3), 2.73 (s, 3H, C6-CH3), 6.29 (q, 1H, J=7.1 Hz, N—CH), 7.3-7.5 (m, 5-H), 7.66 (t, 1H, J=7.7 Hz, H-8), 7.94 (d, 1H, J=6.8 Hz), 8.23 (d, 1H, J=8.2 Hz), 8.43 (s, 1-H), 9.53 (s, 1H, H-10), 16.00 (br s, 1H, COOH).

7-Methoxy-2-methyl-1-oxo-1,2-dihydro-benzo[b][1,6]naphthyridine-4-carboxylic acid (18w)

From 17c and methylamine, as for 18d, and obtained as a yellow solid (86%), mp >300° C. (from dimethyl sulfoxide/1,4-dioxane). $^1$H NMR (d$_6$-DMSO): δ 3.61 (s, 3H, NCH$_3$), 3.99 (s, 3H, ArOCH$_3$), 7.34 (d, J=8.0 Hz, 1H, H-8), 7.54 (S, 1H, H-6), 8.21 (d, J=9.1 Hz, 1H, H-9), 8.73 (s, 1H, H-3), 9.31 (s, 1H, H-10), 15.82 (s, 1H, COOH).

7-Methyl-6-oxo-6,7-dihydropyrido[2,3-b][1,6]naphthyridine-9-carboxylic acid (18y)

From 17e and methylamine, as for 18d except that, after reaction, the volatiles were removed at reduced pressure and water was added. The resultant suspension was stirred and basified with 10% sodium hydroxide, then acidified with concentrated hydrochloric acid (dropwise) and the brown solid was filtered to give 18y, mp >300° C. (from dimethyl sulfoxide/1,4-dioxane). $^1$H NMR (d$_6$-DMSO): δ 3.64 (s, 3H, NCH$_3$), 7.76 (dd, J=8.2, 4.2 Hz, 1H, H-3), 8.81 (d, J=8.2 Hz, 1H, H-4), 8.85 (s, 1H, H-8), 9.28 (dd, J=3.9, 1.7 Hz, 1H, H-2), 9.58 (s, 1H, H-5), 15.68 (s, 1-H, COOH).

2-Methyl-1-oxo-1,2-dihydropyrido[3,4-b]quinoxaline-4-carboxylic acid (18z)

From 17d and methylamine, as for 18d except that, after reaction, the volatiles were removed at reduced pressure to leave the methylamine salt of 18z as a yellow-brown solid. This was suspended in a small amount of water and 10% sodium hydroxide was added dropwise, with stirring, until a solution was obtained. This was acidified with a minimum amount of concentrated hydrochloric acid and the solid which separated was filtered and washed with water to give the free acid as a yellow solid (52%), mp >300° C. (from dimethyl sulfoxide/1,4-dioxane). $^1$H NMR (d$_6$-DMSO): δ 3.66 (s, 3H, NCH$_3$), 7.97 (t, J=7.5 Hz, 1H), 8.08 (t, J=7.6 Hz, 1H), 8.25-8.32 (m, 2H), 8.79 (s, 1H), 14.03 (br s, 1H, COOH).

6-Methyl-1-oxo-1,2-dihydrobenzo[b][1,6]naphthyridine-4-carboxylic acid (18c)

A mixture of 17b (1.0 g) in dimethylformamide (25 mL) was stirred under a stream of ammonia for 4 h at room temperature. The precipitate, which formed after dissolution of the starting material, was collected by filtration and washed thoroughly with acetone to give the ammonium salt of the product as a yellow solid (0.70 g, 78%), mp >300° C. (after forming needles >255° C.). $^1$H NMR (d$_6$-DMSO/CDCl$_3$): δ 2.75 (s, 3H, CH$_3$), 7.16 (t*, 4H, J=51.1 Hz, NH$_4^+$), 7.58 (t, 1H, J=7.6 Hz, H-8), 7.84 (d, 1H, J=6.9 Hz), 8.07 (d, 1H, J=8.3 Hz), 8.37 (d, 1H, J=6.5 Hz, H-3), 9.37 (s, 1H, H-10), 12.20 (br s, 1H, NH), 16.00 (br s, 1H, COOH).

★ Triplet of equal height

The ammonium salt (0.15 g) in 5% hydrochloric acid (20 mL) was heated under reflux until a clear solution was obtained (10 min). After being cooled, the solution was adjusted to pH 4 with 10% sodium hydroxide. The precipitate was collected by filtration to give the acid as a yellow solid (0.13 g, 93%), mp >300° C. (after forming needles >255° C.). $^1$H NMR (d$_6$-DMSO): δ 2.67 (s, 3H, CH$_3$), 7.58 (br s, 1H, H-8), 7.89 (d, 1H, J=4.9 Hz), 8.14 (d, 1H, J=7.0 Hz), 8.31 (s, 1H, H-3), 9.35 (s, 1H, H-10), 12.19 (br s, 1H, NH), 15.90 (br s, 1H, COOH).

Example 3

Preparation of 6-Methyl-1-oxo-2-(2,2,2-trifluoroethyl)-1,2-dihydrobenzo[b][1,6]naphthyridine-4-carboxylic acid (18g)

This is an example of the general preparation of the carboxylic acids of Formula IV from precursor compounds of Formula V by reaction with an amine in the presence of an excess of triethylamine according to Scheme 2b.

To a stirring suspension of dione 17b (1.00 g, 3.54 mmol) in N,N-dimethylformamide (15 mL) was added triethylamine (2.5 mL) with constant stirring. 2,2,2-Trifluoroethylamine (0.40 g, 4.04 mmol) was added and the whole was stirred at room temperature for 16 h. The solid was filtered and washed with water to give the yellow acid (64%), mp 297-300° C. (formed needles at 234-235° C.). $^1$H NMR (d$_6$-DMSO): δ 2.67 (s, 3H, ArCH$_3$), 5.12 (q, J=9.0 Hz, CH$_2$CF$_3$), 7.63 (t, J=7.6 Hz, 1H, H-8), 7.90 (d, J=6.9 Hz, 1H, H-7), 8.17 (d, J=8.2 Hz, 1H, H-9), 8.81 (S, 1H, H-3), 9.46 (S, 1H, H-10), 15.91 (br s, 1H, COOH).

The following compounds were made using a similar procedure.

2-Ethyl-6-methyl-1-oxo-1,2-dihydro-benzo[b][1,6]naphthyridine-4-carboxylic acid (18e)

From 17b and ethylamine, as for 18d except that the initial addition of ethylamine was carried out at 0° C. and a positive pressure of nitrogen was maintained throughout, and obtained as a yellow solid (72%), mp 251-253° C. $^1$H NMR (d$_6$-DMSO): 6.1.30 (t, J=7.1 Hz, 3H, CH$_2$CH$_3$), 2.65 (s, 3H, ArCH$_3$), 4.12 (q, J=7.1 Hz, 2H, CH$_2$CH$_3$), 7.59 (t, J=7.6 Hz, 1H, H-8), 7.86 (d, J=6.8 Hz, 1H, H-7), 8.12 (d, J=8.3 Hz, 1H, H-9), 8.74 (s, 1H, H-3), 9.36 (s, 1H, H-10), 15.89 (s, H-1, COOH).

2-(2-Hydroxyethyl)-6-methyl-1-oxo-1,2-dihydrobenzo[b][1,6]naphthyridine-4-carboxylic acid (18h)

From 17b and ethanolamine, as for 18g, and obtained as a yellow solid (64%), mp 258-261° C. $^1$H NMR (d$_6$-DMSO): δ 2.64 (s, 3H, ArCH$_3$), 3.70 (t, J=6.2 Hz, 2H, CH$_2$CH$_2$OH), 4.15 (t, J=5.0 Hz, 2H, CH$_2$CH$_2$OH), 7.57 (t, J=7.6 Hz, 1H, H-8), 7.85 (d, J=6.8 Hz, 1H, H-7), 8.11 (d, J=8.3 Hz, 1H, H-9), 8.62 (s, 1H, H-3), 9.35 (s, 1H, H-10), 15.85 (s, 1H, COOH).

2-(Ethoxycarbonylmethyl)-6-methyl-1-oxo-1,2-dihydrobenzo[b][1,6]naphthyridine-4-carboxylic acid (18i)

From 17b, triethylamine and glycine ethyl ester hydrochloride, as for 18g except that water was added to the reaction mixture before the acid was filtered. The product was obtained as a yellow solid (65%), mp 277-280° C. $^1$H NMR (d$_6$-DMSO): δ 1.20 (t, J=7.1 Hz, 3H, CO$_2$CH$_2$CH$_3$), 2.69 (s, 3H, ArCH$_3$), 4.17 (q, J=7.1 Hz, 2H, CO$_2$CH$_2$CH$_3$), 4.97 (s, 2H, CH$_2$CO$_2$Et), 7.67 (t, J=7.7 Hz, 1H, H-8), 7.91 (d, J=6.9 Hz, 1H, H-7), 8.18 (d, J=8.2 Hz, 1H, H-9), 8.85 (s, 1H, H-3), 9.44 (s, 1H, H-10), 15.89 (br s, 1H, COOH).

2-(3-Ethoxycarbonylpropyl)-6-methyl-1-oxo-1,2-dihydrobenzo[b][1,6]naphthyridine-4-carboxylic acid (18j)

From 17b and ethyl 4-aminobutyrate hydrochloride, as for 18g except that 1,4-dioxane was used as solvent. After 16 h, water was added to the reaction mixture and the yellow solid was filtered and washed with a little 3% hydrochloric acid, then with water to give the acid 18j (59%), mp 186-188° C. This was used in the next step without further purification but can be recrystallized from toluene as a yellow solid. $^1$H NMR (CDCl$_3$): δ 1.23 (t, J=7.1 Hz, 3H, CO$_2$CH$_2$CH$_3$), 2.15 (quintet, J=7.1 Hz, 2H, CH$_2$CH$_2$CH$_2$), 2.41 (t, J=7.1 Hz, 2H, NCH$_2$CH$_2$CH$_2$), 2.76 (s, 3H, ArCH$_3$), 4.07-4.18 (m, 4H, $CO_2CH_2CH_3$ and $NCH_2CH_2CH_2$), 7.54 (t, J=7.6 Hz, 1H, H-8), 7.77 (d, J=6.9 Hz, 1H, H-7), 7.87 (d, J=8.3 Hz, 1H, H-9), 8.57 (s, 1H, H-3), 9.25 (s, 1H, H-10), 15.93 (s, 1H, COOH). $^{13}$C NMR (CDCl$_3$): δ 14.1 ($CO_2CH_2CH_3$), 18.1 (ArCH$_3$), 24.3 ($CH_2CH_2CH_2$), 31.1 ($NCH_2CH_2CH_2$), 49.3 ($NCH_2CH_2CH_2$), 60.7 ($CO_2CH_2CH_3$), 105.3 (C-4), 118.9 (C-10a), 126.4 (C-9a), 127.4 (CH, C-8), 127.6 (CH, C-9), 134.3 (CH, C-7), 134.8 (C-6), 141.3 (CH, C-10), 145.2 (CH, C-3), 146.5 (C-5a), 148.5 (C-4a), 161.7 (C-1), 166.0 (COOH), 172.1 (CO$_2$Et).

2-(3,4-Dimethoxybenzyl)-6-methyl-1-oxo-1,2-dihydrobenzo[b][1,6]naphthyridine-4-carboxylic acid (18r)

From 17b and veratrylamine, as for 18g, and obtained as a yellow solid (77%), mp 256-257° C. $^1$H NMR (d$_6$-DMSO): δ 2.70 (s, 3H, ArCH$_3$), 3.69 (s, 3H, OCH$_3$), 3.70 (s, 3H, OCH$_3$), 5.25 (s, 2H, CH$_2$Ph), 6.88-6.97 (m, 2H, H-5', H-6'), 7.07 (s, 1H, H-2'), 7.63 (t, J=7.6 Hz, 1H, H-8), 7.90 (d, J=7.0 Hz, 1H, H-7), 8.19 (d, J=8.2 Hz, 1H, H-9), 8.81 (s, 1H, H-3), 9.49 (s, 1H, H-10), 15.97 (br s, 1H, COOH).

2-[2-(3,4-Dimethoxyphenyl)ethyl]-6-methyl-1-oxo-1,2-dihydrobenzo[b][1,6]naphthyridine-4-carboxylic acid (18s)

From 17b and 3,4-dimethoxyphenethylamine, as for 18g, and obtained as a yellow solid (79%), mp 280-282° C. $^1$H NMR (d$_6$-DMSO): δ 2.70 (s, 3H, ArCH$_3$), 2.94 (t, J=7.3 Hz, 2H, CH$_2$CH$_2$Ph), 3.66 (s, 3H, OCH$_3$), 3.67 (s, 3H, OCH$_3$), 4.31 (t, J=7.2 Hz, 2H, CH$_2$CH$_2$Ph), 6.71 (d, J=8.1 Hz, 1H, H-5'), 6.80 (d, J=8.1 Hz, 1H, H-6'), 6.91 (s, 1H, H-2'), 7.64 (t, J=7.8 Hz, 1H, H-8), 7.92 (d, J=6.8 Hz, 1H, H-7), 8.21 (d, J=8.4 Hz, 1H, H-9), 8.67 (s, 1H, H-3), 9.48 (s, 1H, H-10), 15.89 (br s, 1H, COOH).

6-Methyl-1-oxo-2-(pyridin-2-yl)methyl-1,2-dihydrobenzo[b][1,6]naphthyridine-4-carboxylic acid (18t)

From 17b and 2-aminomethylpyridine, as for 18g, and obtained as a yellow solid (57%), mp >300° C. $^1$H NMR (d$_6$-DMSO): δ 2.72 (s, 3H, ArCH$_3$), 5.47 (s, 2H, CH$_2$Pyr), 7.27 (dd, J=7.0, 5.2 Hz, 1H), 7.44 (d, J=7.8 Hz, 1H), 7.63 (t, J=7.6 Hz, 1H), 7.78 (t, J=7.7 Hz, 1H), 7.92 (d, J=6.7 Hz, 1H), 8.18 (d, J=8.3 Hz, 1H), 8.44 (d, J=4.6 Hz, 1H), 8.90 (s, 1H, H-3), 9.43 (s, 1H, H-10), 15.98 (br s, 1H, COOH).

6-Methyl-1-oxo-2-[3-(2-oxopyrrolidin-1-yl)propyl]-1,2-dihydrobenzo[b][1,6]naphthyridine-4-carboxylic acid (18u)

From 17b and N-(3-aminopropyl)-2-pyrrolidinone, as for 18g, and obtained as a yellow solid (0.43 g, 64%), mp 226-228° C. $^1$H NMR (d$_6$-DMSO): δ 1.88-1.89 (m, 4H), 2.20 (t, J=8.0 Hz, 2H), 2.56 (s, 3H, ArCH$_3$), 3.22-3.38 (m, 4H), 4.04 (t, J=7.3 Hz, 2H), 7.54 (t, J=7.7 Hz, 1H, H-8), 7.81 (d, J=7.0 Hz, 1H, H-7), 8.04 (d, J=8.2 Hz, 1H, H-9), 8.74 (s, 1H, H-3), 9.29 (s, 1H, H-10), 15.76 (br s, 1H, COOH).

2-[2-(1H-Indol-3-yl)ethyl]-6-methyl-1-oxo-1,2-dihydrobenzo[b][1,6]naphthyridine-4-carboxylic acid (18v)

From 17b and tryptamine, as for 18g, and obtained as a yellow solid (91%), mp >300° C. $^1$H NMR (d$_6$-DMSO): δ 2.69 (s, 3H, ArCH$_3$), 3.14 (t, J=7.2 Hz, 2H, CH$_2$CH$_2$Indole), 4.36 (t, J=7.1 Hz, 2H, CH$_2$CH$_2$Indole), 6.94 (t, J=7.4 Hz, 1H), 7.02 (t, J=7.5 Hz, 1H), 7.14 (s, 1H, H-2'), 7.30 (d, J=8.0 Hz, 1H), 7.58-7.65 (m, 2H), 7.90 (d, J=6.8 Hz, 1H), 8.19 (d, J=7.9 Hz, 1H), 8.54 (s, 1H, H-3), 9.49 (s, 1H, H-10), 10.83 (s, 1H, NH), 15.91 (s, 1H, COOH).

6-Methyl-1-oxo-2-phenyl-1,2-dihydrobenzo[b][1,6]naphthyridine-4-carboxylic acid (18n)

From 17b and aniline (10 mol equivalents), as for 18g except that the product when filtered was washed thoroughly with acetone. The acid was a lemon coloured solid (41%), mp >310° C., which was used in the next step without further purification but can be recrystallized from 1,4-dioxane. $^1$H NMR (d$_6$-DMSO): δ 2.73 (s, 3H, ArCH$_3$), 7.51-7.59 (m, 5H, Ph), 7.66 (t, J=7.6 Hz, 1H, H-8), 7.95 (d, J=6.9 Hz, 1H, H-7), 8.23 (d, J=8.3 Hz, 1H, H-9), 8.46 (s, 1H, H-3), 9.51 (s, 1H, H-10), 15.99 (br s, 1H, COOH). Anal. Calc. for $C_{20}H_{14}N_2O_3 \cdot 0.4H_2O$: C, 71.2; H, 4.4; N, 8.3% Found: C, 71.3; H, 4.0; N, 8.25%

The filtrate was taken to dryness at reduced pressure, water was added, and the resultant yellow solid was filtered and washed with water to give N,N-Dimethyl-2-[2-(phenylamino)vinyl]-8-methylquinoline-3-carboxamide (32%), mp 143-146° C. (from light petroleum (bp 90-110° C.). $^1$H NMR (d$_6$-DMSO): δ 2.79 (s, 6H, ArCH$_3$ and NCH$_3$), 3.30 (s, 3H, NCH$_3$), 5.31 (d, J=8.5 Hz, 1H, HC=), 6.93 (t, J=7.3 Hz, 1H, H-4'), 7.17 (d, J=8.0 Hz, 2H, H-2', H-6'), 7.30-7.38 (m, 3H, H-6, H-3', H-5'), 7.52-7.62 (m, 2H, =CH, H-7), 7.69 (d, J=7.9 Hz, 1H, H-5), 8.05 (s, 1H, H-4), 11.95 (d, J=11.7 Hz, 1H, NH-exchanges with added D$_2$O). $^{13}$C NMR (d$_6$-DMSO): δ 18.8 (ArCH$_3$), 34.3 (NCH$_3$), 38.2 (NCH$_3$), 94.5 (HC=), 115.0 (2×CH, C-2', C-6'), 121.6 (CH, C-4'), 124.0 (C-4a), 125.0 (CH, C-6), 126.1 (CH, C-5), 129.5 (C, C-3), 129.9 (2×CH, C-3', C-5'), 130.5 (CH, C-7), 133.5 (CH, C-4), 133.7 (C-8), 136.4 (=CH), 141.5 (C-1'), 145.3 (C-8a), 153.8 (C-2), 168.4 (CONMe$_2$). HRMS (EI): Calc. for $C_{21}H_{21}N_3O$: 331.1686. Found: 331.1686.

6-Methyl-1-oxo-2-(4-fluorophenyl)-1,2-dihydrobenzo[b][1,6]naphthyridine-4-carboxylic acid (18o)

From 17b and 4-fluoroaniline (10 mol equivalents), as for 18n. The first filtered product was a triethylamine salt of the target acid. This was dissolved in hot 5% sodium hydroxide, filtered, and the filtrate was cooled and acidified with concentrated hydrochloric acid to give the acid as a yellow solid (26%). $^1$H NMR (d$_6$-DMSO) δ 2.75 (s, 3H, CH$_3$), 7.38-7.43 (m, 2-H), 7.60-7.70 (m, 3-H), 7.95 (d, 1H, J=6.0 Hz), 8.25 (d, 1H, J=8.4 Hz), 8.48 (s, 1-H), 9.53 (s, 1-H).

Addition of water to the first filtrate gave a yellow-green solid which was recrystallized-twice from methanol to give N,N-Dimethyl-2-[2-((4-fluorophenyl)amino)vinyl]-8-methylquinoline-3-carboxamide, mp 172-173° C. after changing form ca 100° C. $^1$H NMR (d$_6$-DMSO): δ 2.78 (s, 3H, CH$_3$) 2.79 and 3.06 (2×s, 6H, N(CH$_3$)$_2$), 5.28 (d, 1H, J=8.5 Hz), 7.13-7.20 (m, 4H), 7.36 (t, 1H, J=7.4 Hz), 7.50 (dd, 1H, J=11.7, 8.5, Hz), 7.61 (d, 1H, J=6.8 Hz), 7.70 (d, 1H, J=7.9 Hz), 8.06 (s, 1H), 11.96 (d, 1H, J=11.7 Hz).

6-Methyl-1-oxo-2-[4-(4,4,5,5-tetramethyl-[1,3,2]dioxaborolan-2-yl)phenyl]-1,2-dihydrobenzo[b][1,6]naphthyridine-4-carboxylic acid (18p)

From 17b and 4-(4,4,5,5-tetramethyl-1,3,2-dioxaborolan-2-yl)aniline, as for 18g. A solution formed slowly and, after 16 h, the volume was reduced to ca ⅓ at reduced pressure, and the whole was cooled on ice. The solid which separated was filtered off, washed with cold toluene and the recrystallized from toluene to give the acid as a yellow solid (20%), mp >300° C. $^1$H NMR (CDCl$_3$): δ 1.40 (s, 12H, 4×CH$_3$), 2.87 (s, 3H, ArCH$_3$), 7.46 (d, J=8.0 Hz, 2H, ArH), 7.61 (t, J=7.6 Hz, 1H, H-8), 7.85 (d, J=6.8 Hz, 1H, H-7), 7.95-8.00 (m, 3H, H-9, ArH), 8.72 (s, 1H, H-3), 9.42 (s, 1H, H-10), 16.16 (s, 1H, COOH).

The filtrate from the reaction mixture (containing DMF, triethylamine and toluene) was taken to dryness at reduced pressure, and the residue was recrystallized from toluene to give the starting aniline as a yellow solid (45% recovery).

2-(3,4-Dimethoxyphenyl)-6-methyl-1-oxo-1,2-dihydrobenzo[b][1,6]naphthyridine-4-carboxylic acid (18q)

A mixture of 4-aminoveratrole (0.12 g), 17b (0.20 g), dimethylformamide (5 mL) and triethylamine (1 mL) was stirred at room temperature for 16 h. Solid was present at all times and it was collected by filtration and washed with a little cold dichloromethane to give 4-[(3,4-dimethoxyphenyl)aminomethylene]-6-methyl-4H-pyrano[4,3-b]quinoline-1,3-dione (19) as a yellow solid (0.25 g, 90%), mp 280-281° C. $^1$H NMR (d$_6$-DMSO): δ 2.81 (s, 3H, CH$_3$), 3.79 (s, 3H, OCH$_3$), 3.87 (s, 3H, OCH$_3$), 7.06 (s, 2H), 7.21 (s, 1H), 7.52 (t, 1H, J=7.5 Hz, H-8), 7.83 (d, 1H, J=7.0 Hz), 8.02 (d, 1H, J=7.9 Hz), 8.81 (s, 1H, J=13.2 Hz, CHN), 9.09 (s, 1H, H-10), 13.83 (d, 1H, J=13.2 Hz, NH).

A mixture of 19 (0.23 g), 4-aminoveratrole (0.46 g), pyridine (15 mL) and triethylamine (1 mL) was heated under reflux for 8 h (dissolution occurred during the heating). The reaction mixture was allowed to stand at −10° C. overnight and the resulting precipitate was collected by filtration and washed with a little cold acetone to give the product as a yellow solid (0.18 g, 78%), mp 297-298° C. (after forming needles->285° C.). $^1$H NMR (d$_6$-DMSO): δ 2.73 (s, 3H, CH$_3$), 3.78 (s, 3H, OCH$_3$), 3.84 (s, 3H, OCH$_3$), 7.12 (s, 2H), 7.23 (s, 1H), 7.67 (t, 1H, J=7.4 Hz, H-8), 7.95 (d, 1H, J=6.7 Hz), 8.23 (d, 1H, J=8.2 Hz), 8.45 (s, 1H), 9.50 (s, 1H, H-10), 15.98 (br s, 1H, COOH).

Example 4

Preparation of 2,2'-[1,3-Propanediylbis[(methylimino)-2,1-ethanediyl]]bis[6-methyl-1-oxo-1,2-dihydrobenzo[b][1,6]naphthyridine-4-carboxylic acid] (18aa).

This is an example of the formation of a bis carboxylic acid precursor to a compound of formula II.

N,N'-Bis-(2-aminoethyl)-N,N'-dimethylpropane-1,3-diamine (0.10 g) was added to a suspension of 17b (0.30 g) in dimethylformamide (7.5 mL) and triethylamine (0.4 mL) and the resulting solution was stirred for 16 h at room temperature. The precipitate, which formed during the reaction, was collected by filtration and was stirred in ethyl acetate (10 mL) for 5 min. The solid was collected by filtration to give the product as a yellow solid (0.15 g, 43%), mp 224-228° C. $^1$H NMR (d$_6$-DMSO): δ 1.45-1.49 (m, 2H), 2.13 (s, 6H, 2×N—CH$_3$), 2.28-2.34 (m, 4H), 2.48-2.55 (m, 10H), 4.01-4.05 (m, 4H), 7.36 (t, 2H, J=7.4 Hz), 7.62 (d, 2H, J=6.5 Hz), 7.93 (d, 2H, J=7.7 Hz), 8.49 (s, 2H), 9.16 (s, 2H).

Example 5

Preparation of N-[2-(Dimethylamino)ethyl]-2,6-dimethyl-1-oxo-1,2-dihydrobenzo[b][1,6]naphthyridine-4-carboxamide (20d).

This is an example of general method A for amide formation according to Scheme 2d.

Acid 18d (0.40 g) was heated under reflux in thionyl chloride (20 mL) for 30 min. The excess of thionyl chloride was removed at reduced pressure and a solution of N,N-dimethylethylenediamine (0.5 mL) in dichloromethane (20 mL) was added to the residue. The resulting solution was stirred at room temperature for 16 h and the solution was washed with 10% sodium hydroxide and water (×2). The solvent was removed at reduced pressure to give the product as a yellow solid (0.48 g, 95%), mp 167-170° C. (from acetonitrile). $^1$H NMR (CDCl$_3$): δ 2.28 (s, 6H, N(CH$_3$)$_2$), 2.61 (t, 2H, J=6.3 Hz), 2.82 (s, 3H, CH$_3$), 3.67-3.73 (m, 5H), 7.46 (t, 1H, J=7.6 Hz, H-8), 7.70 (d, 1H, J=6.9 Hz), 7.82 (d, 1H, J=8.2 Hz), 8.56 (s, 1H, H-3), 9.21 (s, 1H, H-10), 10.91 (br s, 1H, CONH). $^{13}$C NMR (CDCl$_3$): δ 18.5 (C6-CH$_3$), 37.2 (N—CH$_3$), 37.6 (CH$_2$), 45.4 (N(CH$_3$)$_2$), 58.8 (CH$_2$), 109.5 (C), 119.3 (C), 125.9 (C), 126.6 (CH), 127.3 (CH), 132.8 (CH), 135.9 (C), 139.8 (CH), 143.6 (CH), 148.2 (C), 148.8 (C), 162.8 (C), 164.5 (C). ESMS: m/z 339 (M+1).

Anal. Calc. for C$_{19}$H$_{22}$N$_4$O$_2$: C, 67.4; H, 6.6; N, 16.6. Found: C, 67.3; H, 6.6; N, 16.3.

The following amides were made using a similar procedure.

N-[2-(Dimethylamino)ethyl]-2-methyl-1-oxo-1,2-dihydrobenzo[b][1,6]naphthyridine-4-carboxamide (20b)

From acid 18b, and obtained as yellow plates (67%), mp 192-194° C. (from acetonitrile). $^1$H NMR (CDCl$_3$): δ 2.40 (s, 6H, N(CH$_3$)$_2$), 2.63 (t, 2H, J=6.1 Hz), 3.6-3.7 (m, 5-H), 7.60 (t, 1H, J=7.1 Hz), 7.87 (t, 1H, J=7.5 Hz), 8.01 (d, 1H, J=8.2 Hz), 8.10 (d, 1H, J=8.5 Hz), 8.58 (s, 1H), 9.31 (s, 1H, H-10), 11.30 (br s, 1H, CONH). $^{13}$C NMR (CDCl$_3$): δ 36.8 (N—CH$_3$), 37.0 (CH$_2$), 44.9 (N(CH$_3$)$_2$), 57.7 (CH$_2$), 109.0 (C), 119.1 (C), 125.5 (C), 126.4 (CH), 128.0 (CH), 128.8 (CH), 132.5 (CH), 139.1 (CH), 143.2 (CH), 148.5 (C), 149.3 (C), 162.4 (C), 164.0 (C).

Anal. Calc. for C$_{18}$H$_{20}$N$_4$O$_2$: C, 66.7; H, 6.2; N, 17.3. Found: C, 67.1; H, 5.7; N, 17.4.

N-[2-(Dimethylamino)ethyl]-2-butyl-6-methyl-1-oxo-1,2-dihydrobenzo[b][1,6]naphthyridine-4-carboxamide (20f)

From acid 18f, and obtained as a yellow solid (89%), mp 127-128° C. [from light petroleum (bp 90-120° C.)]. $^1$H NMR (CDCl$_3$): δ 0.95 (t, 3H, J=7.3 Hz, CH$_2$—CH$_3$), 1.41 (sextet, 2H, J=7.3 Hz, CH$_2$—CH$_3$), 1.80 (quintet, 2H, J=7.4 Hz, N2-CH$_2$—CH$_2$), 2.29 (s, 6H, N(CH$_3$)$_2$), 2.62 (t, 2H, J=6.5 Hz, CH$_2$—N(CH$_3$)$_2$), 2.85 (s, 3H, C6-CH$_3$), 3.72 (q, 2H, J=6.3 Hz, CONH—CH$_2$), 4.08 (t, 2H, J=7.4 Hz, N2-CH$_2$), 7.47 (t, 1H, J=7.9 Hz, H-8), 7.71 (d, 1H, J=6.8 Hz), 7.85 (d, 1H, J=8.2 Hz), 8.59 (s, 1H, H-3), 9.27 (s, 1H, H-10), 10.97 (br s, 1H, CONH). $^{13}$C NMR (CDCl$_3$): δ 13.6 (CH$_2$—CH$_3$), 18.5 (C6-CH$_3$), 19.8 (CH$_2$), 31.3 (CH$_2$), 37.6 (CH$_2$), 45.4 (N(CH$_3$)

₂), 49.4 (CH₂), 58.8 (CH₂), 109.5 (C), 119.5 (C), 125.9 (C), 126.5 (CH), 127.3 (CH), 132.8 (CH), 135.9 (C), 140.0 (CH), 143.0 (CH), 148.2 (C), 148.8 (C), 162.4 (C), 164.6 (C).

Anal. Calc. for $C_{22}H_{28}N_4O_2$: C, 69.5; H, 7.4; N, 14.7. Found: C, 69.5; H, 7.2; N, 14.7.

N-[2-(Dimethylamino)ethyl]-2-(3-ethoxycarbonyl) propyl-6-methyl-1-oxo-1,2-dihydrobenzo[b][1,6] naphthyridine-4-carboxamide (20j)

From acid 18j, with a reflux time of 5 h, and obtained as a yellow solid (74%), mp 130-132° C. (from toluene/light petroleum (bp 90-120° C.). $^1$H NMR (CDCl₃): δ 1.23 (t, J=7.1 Hz, 3H, CO₂CH₂CH₃), 2.15 (quintet, J=7.2 Hz, 2H, CH₂CH₂CH₂), 2.40 (t, J=7.2 Hz, 2H, NCH₂CH₂CH₂), 2.49 [s, 6H, N(CH₃)₂], 2.84-2.89 (m, 5-H, ArCH₃ and CH₂CH₂NMe₂), 3.84 (q, J=6.2 Hz, 2H, CH₂CH₂NMe₂), 4.07-4.17 (m, 4H, CO₂CH₂CH₃ and NCH₂CH₂CH₂), 7.49 (t, J=7.6 Hz, 1H, H-8), 7.73 (d, J=6.9 Hz, 1H, H-7), 7.86 (d, J=8.2 Hz, 1H, H-9), 8.57 (s, 1H, H-3), 9.27 (s, 1H, H-10), 11.17 (br s, 1H, CONH). $^{13}$C NMR (CDCl₃): δ 14.2 (CO₂CH₂CH₃), 18.6 (ArCH₃), 24.5 (CH₂CH₂CH₂), 31.2 (NCH₂CH₂CH₂), 36.8 (CH₂CH₂NMe₂), 44.7 [N(CH₃)₂], 48.9 (NCH₂CH₂CH₂), 58.0 (CH₂CH₂NMe₂), 60.6 (CO₂CH₂CH₃), 109.5 (C-4), 119.4 (C-10a), 126.0 (C-9a), 126.8 (CH, C-8), 127.4 (CH, C-9), 133.1 (CH, C-7), 135.9 (C-6), 140.1 (CH, C-10), 142.9 (CH, C-3), 148.2 (C-5a), 148.6 (C-4a), 162.4 (C-1), 164.9 (CONH), 172.3 (CO₂Et).

Anal. Calc. for $C_{24}H_{30}N_4O_4 \cdot H_2O$: C, 63.1; H, 7.1; N, 12.3. Found: C, 63.6; H, 7.0; N, 12.3.

N-[2-(Dimethylamino)ethyl]-2-[2-(dimethylamino) ethyl]-6-methyl-1-oxo-1,2-dihydrobenzo[b][1,6] naphthyridine-4-carboxamide (20k)

From acid 18k, and obtained as a yellow solid (84%), mp 141-143° C. [from light petroleum (bp 90-120° C.)]. $^1$H NMR (CDCl₃): δ 2.30 (s, 6H, N(CH₃)₂), 2.38 (s, 6H, N(CH₃)₂), 2.67-2.76 (m, 4H), 2.86 (s, 3H, C6-CH₃), 3.78 (q, 2H, J=6.3 Hz, CH₂), 4.18 (t, 2H, J=6.6 Hz, CH₂), 7.49 (t, 1H, J=7.4 Hz, H-8), 7.73 (d, 1H, J=6.8 Hz), 7.87 (d, 1H, J=8.2 Hz), 8.61 (s, 1H, H-3), 9.29 (s, 1H, H-10), 11.07 (br s, 1H, CONH). $^{13}$C NMR (CDCl₃): δ 18.6 (C6-CH₃), 37.1 (CH₂), 45.0 (N(CH₃)₂), 45.6 (N(CH₃)₂), 47.2 (CH₂), 57.7 (CH₂), 58.5 (CH₂), 109.3 (C), 119.5 (C), 126.0 (C), 126.6 (CH), 127.4 (CH), 133.0 (CH), 135.9 (C), 140.1 (CH), 143.4 (CH), 148.3 (C), 148.8 (C), 162.5 (C), 165.0 (C).

Anal. Calc. for $C_{22}H_{29}N_5O_2 \cdot 0.25H_2O$: C, 66.1; H, 7.4; N, 17.5. Found: C, 66.2; H, 7.6; N, 17.4.

N-[2-(Dimethylamino)ethyl]-2-[2-(dimethylamino) ethyl]-1-oxo-1,2-dihydrobenzo[b][1,6]naphthyridine-4-carboxamide (20l)

From acid 18l, and obtained as a yellow solid (80%), mp 143-144° C. (from toluene). $^1$H NMR (CDCl₃): δ 2.29 (s, 6H, N(CH₃)₂), 2.42 (s, 6H, N(CH₃)₂), 2.65-2.71 (m, 4H), 3.70 (q, 2H, J=6.0 Hz, CH₂), 4.17 (t, 2H, J=6.5 Hz, CH₂), 7.60 (dd, 1H, J=8.4 Hz, 7.4 Hz), 7.88 (t, 1H, J=7.3 Hz), 8.02 (d, 1H, J=8.2 Hz), 8.12 (d, 1H, J=8.6), 8.60 (s, 1H, H-3), 9.32 (s, 1H, H-10), 11.32 (br s, 1H, CONH).

Anal. Calc. for $C_{21}H_{27}N_5O_2$: C, 66.1; H, 7.1; N, 18.4. Found: C, 65.7; H, 7.1; N, 17.9.

(S)-N-[2-(Dimethylamino)ethyl]-6-methyl-1-oxo-2-(1-phenylethyl)-1,2-dihydrobenzo[b][1,6]naphthyridine-4-carboxamide (20m)

From acid 18m, and obtained as a yellow semi-solid (86%). $^1$H NMR (CDCl₃): δ 1.05 (d, 3H, J=7.2 Hz, CH—CH₃), 2.27 (s, 6H, N(CH₃)₂), 2.59 (t, 2H, J=6.5 Hz, CH₂—N(CH₃)₂), 2.85 (s, 3H, C6-CH₃), 3.67 (q, 2H, J=6.7 Hz, CONH—CH₂), 6.45 (q, 1H, J=7.1 Hz, N2-CH), 7.27-7.41 (m, 5H), 7.45 (dd, 1H, J=8.1, 7.3 Hz, H-8), 7.69 (d, 1H, J=7.0 Hz), 7.84 (d, 1H, J=8.2 Hz), 8.62 (s, 1H, H-3), 9.30 (s, 1H, H-10), 10.96 (br s, 1H, CONH). $^{13}$C NMR (CDCl₃): δ 18.5 (CH₃), 19.1 (CH₃), 37.4 (CH₂), 45.4 (N(CH₃)₂), 53.4 (CH), 58.7 (CH₂), 110.0 (C), 119.4 (C), 126.0 (C), 126.5 (CH), 127.2 (CH), 127.3 (CH), 128.2 (CH), 128.9 (CH), 132.8 (CH), 135.9 (C), 139.56 (CH), 139.61 (CH), 140.3 (CH), 148.2 (C), 148.4 (C), 162.4 (C), 164.6 (C). HRMS (LSI): Calc. for $C_{26}H_{29}N_4O_2$ [(M+H)]: 429.2292. Found: 429.2298.

N-[2-(Dimethylamino)ethyl]-6-methyl-2-phenyl-1-oxo-1,2-dihydrobenzo[b][1,6]naphthyridine-4-carboxamide (20n)

From acid 18n, and obtained as pale yellow needles (55%), mp 199-201° C. (from methanol). $^1$H NMR (CDCl₃): δ 2.35 [s, 6H, N(CH₃)₂], 2.70 (t, J=6.4 Hz, 2H, CH₂CH₂NMe₂), 2.88 (s, 3H, ArCH₃), 3.77 (q, J=6.1 Hz, 2H, CH₂CH₂NMe₂), 7.43-7.55 (m, 6H, H-8, Ph), 7.75 (d, J=6.9 Hz, 1H, H-7), 7.88 (d, J=8.1 Hz, 1H, H-9), 8.71 (s, 1H, H-3), 9.32 (s, 1H, H-10), 11.06 (br s, 1H, CONH). $^{13}$C NMR (CDCl₃) δ 18.6 (ArCH₃), 37.5 (CH₂CH₂NMe₂), 45.3 [N(CH₃)₂], 58.6 (CH₂CH₂NMe₂), 110.0 (C-4), 119.9 (C-10a), 126.2 (C-9a), 126.7 (2×CH, Ph), 126.8 (CH, C-8), 127.4 (CH, C-9), 128.8 (CH, C-4'), 129.5 (2×CH, Ph), 133.1 (CH, C-7), 136.1 (C-6), 140.1 (C-1'), 140.5 (CH, C-10), 143.4 (CH, C-3), 148.4 (C-5a), 148.9 (C-4a), 162.2 (C-1), 164.6 (CONH).

Anal. Calc. for $C_{24}H_{24}N_4O_2$: C, 72.0; H, 6.0; N, 14.0. Found: C, 71.8; H, 6.0; N, 13.75.

N-[2-(Dimethylamino)ethyl]-2-(4-fluorophenyl)-6-methyl-1-oxo—1,2-dihydrobenzo[b][1,6]naphthyridine-4-carboxamide (20o)

From acid 18o, and obtained as pale yellow needles (88%), mp 219-220° C. (from acetonitrile). $^1$H NMR (CDCl₃): δ 2.45 (s, 6H, N(CH₃)₂), 2.82 (t, 2H, J=6.3 Hz, CH₂—N(CH₃)₂), 2.87 (s, 3H, C6-CH₃), 3.83 (q, 2H, J=6.4 Hz, CONH—CH₂), 7.18-7.25 (m, 2H), 7.42-7.55 (m, 3H), 7.76 (d, 1H, J=7.0 Hz), 7.89 (d, 1H, J=8.1 Hz), 8.65 (s, 1H, H-3), 9.30 (s, 1H, H-10), 11.14 (br s, 1H, CONH). $^{13}$C NMR (CDCl₃): δ 18.4 (C6-CH₃), 35.7 (CH₂), 43.7 (N(CH₃)₂), 56-9 (CH₂), 109.1 (C), 116.15 (d, J=23.1 Hz, C3', 5'-H), 119.2 (C), 125.8 (C), 126.8 (CH), 127.0 (CH), 128.16 (d, J=8.5 Hz, C2', 6'-H), 133.2 (CH), 135.5 (C), 140.3 (CH), 142.8 (CH), 147.8 (C), 148.0 (C), 161.8 (C), 162.0 (d, J=244.5 Hz, C4'), 164.8 (C).

Anal. Calc. for $C_{24}H_{23}FN_4O_2$: C, 68.9; H, 5.5; N, 13.4. Found: C, 68.9; H, 5.6; N, 13.4.

N-[2-(Dimethylamino)ethyl]-2-(3,4-dimethoxyphenyl)-6-methyl-1-oxo-1,2-dihydrobenzo[b][1,6]naphthyridine-4-carboxamide (20g)

From acid 18q, and obtained as a yellow solid (92%), mp 199-201° C. (from toluene). $^1$H NMR (CDCl₃): δ 2.35 (s, 6H, N(CH₃)₂), 2.70 (t, 2H, J=6.3 Hz, CH₂—N(CH₃)₂), 2.89 (s, 3H, C6-CH₃), 3.77 (q, 2H, J=6.4 Hz, CONH—CH₂), 3.90 (s, 3H, OCH₃), 3.94 (s, 3H, OCH₃), 6.96-6.99 (m, 3H), 7.52 (t, 1H, J=7.5 Hz, H-8), 7.76 (d, 1H, J=7.0 Hz), 7.89 (d, 1H, J=8.1 Hz), 8.71 (s, 1H, H-3), 9.34 (s, 1H, H-10), 11.07 (br s, 1H, CONH). $^{13}$C NMR (CDCl$_3$): δ 18.6 (C6-CH$_3$), 37.3 (CH$_2$), 45.2 [N(CH$_3$)$_2$], 56.1 (2×OCH$_3$), 58.5 (CH$_2$), 109.7 (C), 110.6 (CH), 111.2 (CH), 118.9 (CH), 119.8 (C), 126.1 (C), 126.9 (CH), 127.4 (CH), 133.0 (C), 133.2 (CH), 136.0 (C), 140.5 (CH), 143.8 (CH), 148.4 (C), 148.6 (C), 149.3 (C), 149.4 (C), 162.5 (C), 164.7 (C).

Anal. Calc. for C$_{26}$H$_{28}$N$_4$O$_4$.0.5H$_2$O: C, 66.5; H, 6.2; N, 11.9. Found: C, 66.2; H, 6.4; N, 11.3.

N-[2-(Dimethylamino)ethyl]-6-chloro-7-methoxy-2-methyl-1-oxo-1,2-dihydro-benzo[b][1,6]naphthyridine-4-carboxamide (20x)

From acid 18w, with a reflux time of 5 h, and obtained as a brown solid (73%), mp 209-212° C. (from acetonitrile). $^1$H NMR (CDCl$_3$): δ 2.32 [s, 6H, N(CH$_3$)$_2$], 2.69 (t, J=6.8 Hz, 2H, CH$_2$CH$_2$NMe$_2$), 3.69-3.77 (m, 5H, CH$_2$CH$_2$NMe$_2$ and NCH$_3$), 4.14 (s, 3H, ArOCH$_3$), 7.45 (d, J=9.2 Hz, 1H), 7.97 (d, J=9.2 Hz, 1H), 8.63 (s, 1H, H-3), 9.24 (s, 1H, H-10), 11.17 (br s, 1H, CONH). $^{13}$C NMR (CDCl$_3$): δ 37.2 (CH$_3$), 37.9 (CH$_2$), 45.6 [N(CH$_3$)$_2$]$_1$, 57.0 (CH$_3$), 58.9 (CH$_2$), 109.4 (C), 114.4 (CH), 116.6 (C), 118.2 (C), 121.9 (C), 129.1 (CH), 139.9 (CH), 144.5 (CH), 146.1 (C), 150.5 (C), 158.3 (C), 162.6 (C), 164.3 (C).

Anal. Calc. for C$_{19}$H$_{21}$ClN$_4$O$_3$C, 58.7; H, 5.4; N, 14.4. Found: C, 58.3; H, 5.4; N, 14.3.

N-[2-(Dimethylamino)ethyl]-7-methyl-6-oxo-6,7-dihydropyrido[2,3-b][1,6]naphthyridine-9-carboxamide (20y)

From acid 18y, with a reflux time of 1.5 h (complete dissolution did not occur). The crude amide was added to a short silica column. This was first eluted with dichloromethane/methanol (19:1) and then with dichloromethane/methanol (1:1) which furnished the amide as a yellow solid (17%), mp 218-221° C. (from acetonitrile). $^1$H NMR (CDCl$_3$): δ 2.41 [s, 6H, N(CH$_3$)$_2$], 2.74 (t, J=6.6 Hz, 2H, CH$_2$CH$_2$NMe$_2$), 3.70 (s, 3H, ArCH$_3$), 3.76 (q, J=6.3 Hz, 2H, CH$_2$CH$_2$NMe$_2$), 7.57 (dd, J=8.2, 4.2 Hz, 1H, H-3), 8.40 (dd, J=8.3, 2.0 Hz, 1H, H-4), 8.68 (s, 1H, H-8), 9.27 (dd, J=4.2, 2.0, 1H, H-2), 9.36 (s, 1H, H-5), 10.95 (br s, 1H, CONH). $^{13}$C NMR (CDCl$_3$): δ 37.0 (NCH$_3$), 37.3 (CH$_2$CH$_2$NMe$_2$), 45.1 [N(CH$_3$)$_2$], 58.2 (CH$_2$CH$_2$NMe$_2$), 109.1 (C-9), 120.1 (C), 120.4 (C), 122.1 (CH, C-3), 138.3 (CH, C-4), 141.4 (CH, C-5), 145.0 (CH, C-8), 152.1 (C-9a), 155.2 (C-10a), 157.2 (CH, C-2), 161.9 (C-6), 163.7 (CONH).

Anal. Calc. for C$_{17}$H$_{19}$N$_5$O$_2$.H$_2$O: C, 59.5; H, 6.2; N, 20.4. Found: C, 59.6; H, 5.7; N, 20.3%.

N-[2-(Dimethylamino)ethyl]-2-methyl-1-oxo-1,2-dihydropyrido[3,4-b]quinoxaline-4-carboxamide (20z)

From acid 18z, with a reflux time of 45 min., and obtained as golden flakes (47%), mp 215-218° C. (after forming needles >109° C.) (from acetonitrile). $^1$H NMR (CDCl$_3$): δ 2.41 [s, 6H, N(CH$_3$)$_2$], 2.65 (t, J=6.1 Hz, 2H, CH$_2$CH$_2$NMe$_2$), 3.67 (q, J=5.7 Hz, 2H, CH$_2$CH$_2$NMe$_2$), 3.75 (s, 3H, NCH$_3$), 7.80-7.86 (m, 1H), 7.88-7.95 (m, 1H), 8.08 (d, J=8.3 Hz, 1H), 8.38 (d, J=8.1 Hz, 1H), 8.63 (s, 1H), 10.61 (br s, 1H). $^{13}$C NMR (CDCl$_3$): δ 37.1 (CH$_2$), 37.5 (CH$_3$), 44.9 [N(CH$_3$)$_2$], 57.5 (CH$_2$), 108.0 (C), 127.9 (CH), 130.4 (CH), 130.5 (CH), 133.3 (CH), 136.7 (C), 141.4 (C), 142.2 (C), 143.5 (CH), 144.9 (C), 160.9 (C), 163.2 (C).

The hydrochloride had mp 218-221° C. (from ethanol).

2,2'-[1,3-Propanediylbis[(methylimino)-2,1-ethanediyl]]bis [N-(2-(dimethylamino)ethyl)-6-methyl-1-oxo-1,2-dihydrobenzo[b][1,6]naphthyridine-4-carboxamide (20aa)

From acid 18aa, and obtained as a yellow solid (75%), mp 97-102° C. [from light petroleum (bp 90-120° C.)]. $^1$H NMR (CDCl$_3$): δ 1.55-1.63 (m, 2H), 2.23 (s, 6-H), 2.42-2.84 [m, 30-H, incl. 2.50 (s, 12H), 2.72 (s, 6-H)], 3.78 (q, 4H, J=6.2 Hz, CH$_2$), 4.08 (t, 4H, J=5.9 Hz, CH$_2$), 7.31 (t, 2H, J=7.8 Hz), 7.53 (d, 2H, J=6.8 Hz), 7.71 (d, 2H, J=8.2 Hz), 8.51 (s, 2H), 9.11 (s, 2H), 10.96 (br s, 2H, 2×CONH). $^{13}$C NMR (CDCl$_3$): δ 18.5 (CH$_3$), 24.8 (CH$_2$), 36.9 (CH$_2$), 42.1 (NCH$_3$), 44.9 (N(CH$_3$)$_2$), 46.8 (CH$_2$), 54.9 (CH$_2$), 56.5 (CH$_2$), 58.2 (CH$_2$), 108.6 (C), 119.2 (C), 125.6 (C), 126.4 (CH), 127.1 (CH), 132.6 (CH), 135.6 (C), 139.7 (CH), 143.8 (CH), 147.8 (C), 148.4 (C), 162.1 (C), 164.8 (C).

ESMS: m/z 402.3 [(M+2)/2, 100%], 803.5 (M+1, 50%).

Anal. Calc. for C$_{45}$H$_{58}$N$_{10}$O$_4$.1.5H$_2$O: C, 65.1; H, 7.4; N, 16.9. Found: C, 65.5; H, 7.2; N, 16.3.

(S)-N-[1-((Dimethylamino)carbonyl)ethyl]-2,6-dimethyl-1-oxo-1,2-dihydrobenzo[b][1,6]naphthyridine-4-carboxamide (20bb)

From acid 18d, with a reflux time of 45 min. To the residue from removal of the thionyl chloride was added triethylamine (2.2 mol equivalents) in dichloromethane followed by (S)-2-amino-N,N-dimethylpropanamide (1.1 mol equivalents) in dichloromethane. The standard reaction and work up gave the amide (88%) as yellow needles, mp 268-274° C. (from acetonitrile). $^1$H NMR (d$_6$-DMSO, 100° C.): δ 1.42 (d, J=6.8 Hz, 3H, CHCH$_3$), 2.81 (s, 3H, ArCH$_3$), 2.99 [br s, 6H, N(CH$_3$)$_2$], 3.62 (s, 3H, NCH$_3$), 5.21 (quintet, J=7.1 Hz, 1H, CHCH$_3$), 7.53 (t, J=7.6 Hz, 1H, H-8), 7.79 (d, J=6.8 Hz, 1H, H-7), 8.03 (d, J=8.2 Hz, 1H, H-9), 8.55 (s, 1H, H-3), 9.26 (s, 1H, H-10), 10.84 (br d, J=7.7 Hz, 1H, CONH). $^{13}$C NMR (d$_6$-DMSO, 100° C.): δ 18.2 (ArCH$_3$), 18.4 (CHCH$_3$), 36.1 [br s, N(CH$_3$)$_2$], 36.5 (NCH$_3$), 44.6 (CHCH$_3$), 108.6 (C-4), 119.1 (C-10a), 125.8 (C-9a), 126.6 (CH, C-8), 127.5 (CH, C-9), 133.0 (CH, C-7), 135.7 (C-6), 139.6 (CH, C-10), 144.7 (CH, C-3), 147.8 (C-5a), 148.7 (C-4a), 162.0 (C-1), 162.8 (CONH), 172.1 (CONMe$_2$).

The hydrochloride had mp 277-280° C. (yellow needles from ethanol).

(S)-N-[2-(1-Dimethylamino)propyl]-2,6-dimethyl-1-oxo-1,2-dihydrobenzo[b][1,6]naphthyridine-4-carboxamide (20 cc)

From acid 18d, with a reflux time of 45 min. To a suspension in dichloromethane of the residue from removal of the thionyl chloride was added a solution of (S)—N$^1$,N$^1$-dimethylpropane-1,2-diamine hydrochloride (2.2 mol equivalents) and triethylamine (2.2 mol equivalents) in dichloromethane. The standard reaction and work up gave the amide (38%) as a light brown solid, mp 205-209° C. (from acetonitrile). $^1$H NMR (d$_6$-DMSO, 100° C.): δ 1.46 (d, J=6.6 Hz, 3H, CHCH$_3$), 2.81 (s, 3H, ArCH$_3$), 2.84 [s, 6H, N(CH$_3$)$_2$], 3.31 (d, J=6.8 Hz, 2H, CH$_2$NMe$_2$), 3.64 (s, 3H, NCH$_3$), 4.64 (quintet, J=6.9 Hz, 1H, CHCH$_3$), 7.57 (t, J=7.6 Hz, 1H, H-8), 7.84 (d, J=6.0 Hz, 1H, H-7), 8.08 (d, J=8.1 Hz, 1H, H-9), 8.60 (s, 1H, H-3), 9.31 (s, 1H, H-10), 10.75 (br s, 1H, CONH). $^{13}$C NMR ($d_6$-DMSO, 100° C.): δ 18.5 (ArCH$_3$), 19.6 (CHCH$_3$), 36.6 (NCH$_3$), 43.4 [N(CH$_3$)$_2$], 62.4 (CH$_2$NMe$_2$), 108.4 (C-4), 119.2 (C-10a), 125.9 (C-9a), 126.8 (CH, C-8), 127.7 (CH, C-9), 133.3 (CH, C-7), 135.2 (C-6), 139.8 (CH, C-10), 144.9 (CH, C-3), 147.7 (C-5a), 148.7 (C-4a), 162.0 (C-1), 164.2 (CONH). CHCH$_3$ was not observed.

The hydrochloride had mp 251-254° C. after forming needles >200° C. (mustard powder from acetonitrile).

N-[(2-Dimethylamino)ethyl]-6-methyl-1-oxo-1,2-dihydrobenzo[b][1,6]naphthyridine-4-carboxamide perchlorate salt (20c)

From the ammonium salt of 18c, and obtained in crude form as a yellow solid (69%). The perchlorate salt was prepared in ethanol, recrystallized from 'moist' methanol, and obtained as a brown solid, mp 218-219° C. (explosive decomposition >250° C.). $^1$H NMR ($d_4$-MeOD): δ 2.91 (s, 9-H, C6-CH$_3$+N(CH$_3$)$_2$), 3.19 (t, 2H, J=6.2 Hz, CH$_2$), 3.45 (t, 2H, J=6.2 Hz), 6.96-7.00 (m, 2H), 7.21 (br s, 1H), 7.37 (br s, 1H), 7.67 (br s, 1H). ESMS: m/z 325 (M+1, 100%), 163 [(M+2)/2, 12%].

Anal. Calc. for C$_{18}$H$_{20}$N$_4$O$_2$·HClO$_4$·2H$_2$O: C, 46.9; H, 5.5; N, 12.2. Found: C, 46.6; H, 5.2; N, 12.6.

Example 6

Preparation of N-[2-(Dimethylamino)ethyl]-2-ethyl-6-methyl-1-oxo-1,2-dihydrobenzo[b][1,6]-naphthyridine-4-carboxamide (20e)

This is an example of general method B for amide formation according to Scheme 2d.

A mixture of acid 18e (0.23 g, 0.81 mmol) and 1,1'-carbonyldiimidazole (CDI) (0.66 g, 4.07 mmol) in 1,4-dioxane (15 mL) was heated under reflux for 24 h, during which time dissolution occurred. The solvent was removed at reduced pressure and to the residue was added, N,N-dimethylethylenediamine (1 mL) in dichloromethane (25 mL). The solution was then stirred for 16 h at room temperature. More dichloromethane was added and the solution was washed with 10% sodium hydroxide (×1) and water (×3). The organic fraction was dried over magnesium sulphate and the solvent was removed at reduced pressure to give the amide 20e as a bright yellow solid (0.26 g, 91%), mp 157-158° C. (from acetonitrile). $^1$H NMR (CDCl$_3$): δ 1.37 (t, J=7.2 Hz, 3H, CH$_2$CH$_3$), 2.23 [s, 6H, N(CH$_3$)$_2$], 2.54 (t, J=6.5 Hz, 2H, CH$_2$CH$_2$NMe$_2$), 2.66 (s, 3H, ArCH$_3$), 3.63 (q, J=6.2 Hz, 2H, CH$_2$CH$_2$NMe$_2$), 4.05 (q, J=7.2 Hz, 2H, CH$_2$CH$_3$), 7.32 (dd, J=8.0, 7.2 Hz, 1H, H-8), 7.55 (d, J=6.9 Hz, 1H, H-7), 7.65 (d, J=8.2 Hz, H-1, H-9), 8.48 (s, 1H, H-3), 8.99 (s, 1H, H-10), 10.73 (br t, J=5.1 Hz, CONH). $^{13}$C NMR (CDCl$_3$): δ 14.4 (CH$_2$CH$_3$), 18.3 (ArCH$_3$), 37.5 (CH$_2$CH$_2$NMe$_2$), 44.6 (CH$_2$CH$_3$), 45.3 [N(CH$_3$)$_2$], 58.7 (CH$_2$CH$_2$NMe$_2$), 109.5 (C-4), 119.2 (C-10a), 125.5 (C-9a), 126.2 (CH, C-8), 127.1 (CH, C-9), 132.4 (CH, C-7), 135.6 (C-6), 139.4 (CH, C-10), 142.4 (CH, C-3), 147.7 (C-5a), 148.4 (C-4a), 161.9 (C-1), 164.3 (CONH).

Anal. Calc. for C$_{20}$H$_{24}$N$_4$O$_2$C, 68.2; H, 6.9; N, 15.9. Found: C, 68.5; H, 6.8; N, 16.1.

The following compounds were prepared in a similar manner:

N-[2-(Dimethylamino)ethyl]-6-methyl-1-oxo-2-(2,2,2-trifluoroethyl)-1,2-dihydrobenzo[b][1,6]naphthyridine-4-carboxamide (20g)

From acid 18g, and obtained as a yellow solid (83%), mp 227-230° C. (from acetonitrile). $^1$H NMR (CDCl$_3$): δ 2.30 [s, 6H, N(CH$_3$)$_2$], 2.63 (t, J=6.4 Hz, 2H, CH$_2$CH$_2$NMe$_2$), 2.85 (s, 3H, ArCH$_3$), 3.72 (q, J=6.1 Hz, 2H, CH$_2$CH$_2$NMe$_2$), 4.73 (q, J=8.4 Hz, 2H, CH$_2$CF$_3$), 7.51 (t, J=7.6 Hz, 1H, H-8), 7.74 (d, J=6.9 Hz, 1H, H-7), 7.85 (d, J=8.2 Hz, H-1, H-9), 8.58 (s, 1H, H-3), 9.27 (s, 1H, H-10), 10.84 (br s, 1H, CONH). $^{13}$C NMR (CDCl$_3$): δ 18.4 (ArCH$_3$), 37.8 (CH$_2$CH$_2$NMe$_2$), 45.4 [N(CH$_3$)$_2$], 48.3 (q, J=35.3 Hz, CH$_2$CF$_3$), 58.8 (CH$_2$CH$_2$NMe$_2$), 111.3 (C-4), 119.1 (C-10a), 123.4 (q, J=280 Hz, CH$_2$CF$_3$), 126.3 (C-9a), 127.2 (CH, C-8), 127.4 (CH, C-9), 133.4 (CH, C-7), 136.3 (C-6), 140.6 (CH, C-10), 142.1 (CH, C-3), 148.6 (C-5a), 148.7 (C-4a), 162.3 (C-1), 164.0 (CONH).

Anal. Calc. for C$_{20}$H$_{21}$F$_3$N$_4$O$_2$: C, 59.1; H, 5.2; N, 13.8. Found: C, 59.4; H, 5.4; N, 13.9.

N-[2-(Dimethylamino)ethyl]-2-(ethoxycarbonylmethyl)-6-methyl-1-oxo-1,2-dihydrobenzo[b][1,6]-naphthyridine-4-carboxamide (20i)

From acid 18i with a reflux time of 48 h and a recharge with an equal amount of CDI after 24 h, and obtained as a yellow solid (79%), mp 214-215° C. (from acetonitrile). $^1$H NMR (CDCl$_3$): δ 1.28 (t, J=7.2 Hz, 3H, CO$_2$CH$_2$CH$_3$), 2.29 [s, 6H, N(CH$_3$)$_2$], 2.62 (t, J=6.4 Hz, 2H, CH$_2$CH$_2$NMe$_2$), 2.87 (s, 3H, ArCH$_3$), 3.72 (q, J=5.9 Hz, CH$_2$CH$_2$NMe$_2$), 4.25 (q, J=7.1 Hz, CO$_2$CH$_2$CH$_3$), 4.78 (s, 2H, CH$_2$CO$_2$Et), 7.51 (t, J=7.6 Hz, 1H, H-8), 7.74 (d, J=6.9 Hz, 1H, H-7), 7.87 (d, J=8.2 Hz, 1H, H-9), 8.53 (s, 1H, H-3), 9.28 (s, 1H, H-10), 10.96 (br t, J=4.8 Hz, 1H, CONH). $^{13}$C NMR (CDCl$_3$): δ 13.7 (CO$_2$CH$_2$CH$_3$), 18.1 (ArCH$_3$), 37.3 (CH$_2$CH$_2$NMe$_2$), 45.1 [N(CH$_3$)$_2$], 50.1 (CH$_2$CO$_2$Et), 58.4 (CH$_2$CH$_2$NMe$_2$), 61.6 (CO$_2$CH$_2$CH$_3$), 109.8 (C-4), 118.7 (C-10a), 125.5 (C-9a), 126.4 (CH, C-8), 126.9 (CH, C-9), 132.6 (CH, C-7), 135.6 (C-6), 139.6 (CH, C-10), 142.7 (CH, C-3), 147.8 (C-5a), 148.4 (C-4a), 162.0 (C-1), 163.9 (CONH), 166.9 (CO$_2$Et).

Anal. Calc. for C$_{22}$H$_{26}$N$_4$O$_4$: C, 64.4; H, 6.4; N, 13.65. Found: C, 64.5; H, 6.4; N, 13.9.

N-[2-(Dimethylamino)ethyl]-2-(4-boronophenyl)-6-methyl-1-oxo-1,2-dihydrobenzo[b][1,6]naphthyridine-4-carboxamide (20p)

From acid 18p, carried out under nitrogen, with a reflux time of 48 h and a recharge with an equal amount of CDI after 24 h. When the amination reaction was complete, the volatiles were removed at reduced pressure with heat (~0.3 mmHg, 100° C., 20 min) and residual N,N-dimethylethylenediamine was removed by azeotropic distillation with toluene (×3). The residue was then boiled in toluene and, while hot, decanted from a brown oil. The toluene was removed at reduced pressure, and the residue was recrystallized from acetonitrile to give the intermediate N-[2-(dimethylamino)ethyl]-6-methyl-1-oxo-2-[4-(4,4,5,5-tetramethyl-[1,3,2]dioxaborolan-2-yl)phenyl]1,2-dihydrobenzo[b][1,6]naphthyridine-4-carboxamide as a yellow solid (74%), mp 139-141° C. $^1$H NMR (CDCl$_3$): δ 1.34 (s, 12H, 4×CH$_3$), 2.31 [s, 6H, N(CH$_3$)$_2$], 2.64 (t, J=6.5 Hz, 2H, CH$_2$CH$_2$NMe$_2$), 2.81 (s, 3H, ArCH$_3$), 3.72 (q, J=6.1 Hz, 2H, CH$_2$CH$_2$NMe$_2$), 7.42-7.48 (m, 3H, H-8,2', 6'), 7.69 (d, J=6.9 Hz, 1H, H-7), 7.80 (d, J=8.1 Hz, 1H, H-9), 7.95 (d, J=8.3 Hz, 2H, H-3', 5'), 8.68 (s, 1H, H-3), 9.23 (s, 1H, H-10), 10.98 (br t, J=5.4 Hz, 1H, CONH). $^{13}$C NMR (CDCl$_3$):

δ 18.2 (ArCH$_3$), 24.5 (4×CH$_3$)$_1$ 37.2 (CH$_2$CH$_2$NMe$_2$), 45.0 [N(CH$_3$)$_2$], 58.3 (CH$_2$CH$_2$NMe$_2$), 83.8 (2×C), 109.7 (C-4), 119.4 (C-10a), 125.5 (2×CH, C-2', 6'), 125.7 (C-9a), 126.4 (CH, C-8), 127.0 (CH, C-9), 132.7 (CH, C-7), 135.6 (2×CH, C-3', 5'), 140.1 (CH, C-10), 142.0 (C-1'), 142.8 (CH, C-3), 147.8 (C-5a), 148.4 (C-4a), 161.7 (C-1), 164.1 (CONH). C-6 and C-4' were not observed.

Water (5 mL) was added to a solution of this compound (0.12 g, 0.23 mmol) in methanol (5 mL), and the whole was heated at reflux for 30 min. The volume was then reduced to ca ~2 mL) at reduced pressure, water was added, and the solid was filtered, washed with water and recrystallized from ethanol to give the boronic acid 20p as a yellow solid (0.05 g, 49%), mp 242-244° C. $^1$H NMR (d$_6$-DMSO): δ 2.23 [s, 6H, N(CH$_3$)$_2$], 2.56 (t, J=5.8 Hz, 2H, CH$_2$CH$_2$NMe$_2$), 2.82 (s, 3H, ArCH$_3$), 3.59 (q, J=5.7 Hz, 2H, CH$_2$CH$_2$NMe$_2$), 7.52 (d, J=8.0 Hz, 2H, H-3', 5'), 7.59 (t, J=7.5 Hz, 1H, H-8), 7.86 (d, J=6.7 Hz, 1H, H-7), 7.95 (d, J=8.0 Hz, 2H, H-2', 6'), 8.14 (d, J=8.0 Hz, 1H, H-9), 8.23 [s, 2H, B(OH)$_2$], 8.43 (s, 1H, H-3), 9.39 (s, 1H, H-10), 10.76 (br t, J=4.8 Hz, 1H, CONH). $^{13}$C NMR (d$_6$-DMSO): δ 17.8 (ArCH$_3$), 37.1 (CH$_2$CH$_2$NMe$_2$), 45.1 [N(CH$_3$)$_2$], 58.5 (CH$_2$CH$_2$NMe$_2$), 109.2 (C-4), 119.5 (C-10a), 125.7 (C-9a), 125.8 (C-2', 6'), 126.8 (CH, C-8), 127.6 (CH, C-9), 133.2 (CH, C-7), 135.1 (C-3', 5'), 135.3 (C-6), 140.1 (CH, C-10), 141.8 (C-1'), 143.2 (CH, C-3), 147.4 (C-5a), 148.4 (C-4a), 161.3 (C-1), 163.2 (CONH). C-4' was not observed.

Anal. Calc. for C$_{24}$H$_{25}$BN$_4$O$_4$: C, 64.9; H, 5.9; N, 12.5. Found: C, 64.4; H, 5.9; N, 12.5.

N-[2-(Dimethylamino)ethyl]-2-(3,4-dimethoxybenzyl)-6-methyl-1-oxo-1,2-dihydrobenzo[b][1,6]naphthyridine-4-carboxamide (20r)

From acid 18r with a reflux time of 48 h and a recharge with an equal amount of CDI after 24 h, and obtained as a yellow solid (85%), mp 213-214° C. (from acetonitrile). $^1$H NMR (CDCl$_3$): δ 2.22 [s, 6H, N(CH$_3$)$_2$]1, 2.52 (t, J=6.4 Hz, 2H, CH$_2$CH$_2$NMe$_2$), 2.63 (s, 3H, ArCH$_3$), 3.62 (q, J=6.1 Hz, 2H, CH$_2$CH$_2$NMe$_2$), 3.75 (s, 3H, OCH$_3$), 3.78 (s, 3H, OCH$_3$), 5.09 (s, 2H, CH$_2$Ph), 6.74 (d, J=8.5 Hz, 1H, H-5'), 6.90-6.92 (m, 2H, H-2', H-6'), 7.27 (t, J=7.6 Hz, 1H, H-8), 7.49 (d, J=6.8 Hz, 1H, H-7), 7.61 (d, J=8.1 Hz, 1H, H-9), 8.55 (s, 1H, H-3), 8.99 (s, 1H, H-10), 10.70 (br t, J=5.3 Hz, 1H, CONH). $^{13}$C NMR (CDCl$_3$) δ 18.2 (ArCH$_3$), 37.4 (CH$_2$CH$_2$NMe$_2$), 45.2 [N(CH$_3$)$_2$], 51.9 (CH$_2$Ph), 55.6 (OCH$_3$), 55.7 (OCH$_3$), 58.6 (CH$_2$CH$_2$NMe$_2$), 109.6 (C-4), 111.1 (CH, C-5'), 111.5 (CH, C-6'), 119.1 (C-10a), 120.9 (CH, C-2'), 125.4 (C-9a), 126.2 (CH, C-8), 126.9 (CH, C-9), 128.2 (C-1'), 132.4 (CH, C-7), 135.5 (C-6), 139.5 (CH, C-10), 142.3 (CH, C-3), 147.6 (C-5a), 148.2 (C-4a), 148.9 (C-4'), 149.1 (C-3'), 162.1 (C-1), 164.1 (CONH).

Anal. Calc. for C$_{27}$H$_{30}$N$_4$O$_4$C, 68.3; H, 6.4; N, 11.8. Found: C, 68.5; H, 6.6; N, 11.8.

N-[2-(Dimethylamino)ethyl]-2-[2-(3,4-dimethoxyphenyl)ethyl]-6-methyl-1-oxo-1,2-dihydrobenzo[b][1,6]naphthyridine-4-carboxamide (20s)

From acid 18s with a reflux time of 48 h and a recharge with an equal amount of CDI after 24 h, and obtained as a yellow solid (81%), mp 113-114° C. (from acetonitrile). $^1$H NMR (CDCl$_3$): δ 2.26 [s, 6H, N(CH$_3$)$_2$], 2.58 (t, J=6.5 Hz, 2H, CH$_2$CH$_2$NMe$_2$), 2.77 (s, 3H, ArCH$_3$), 3.01 (m, 2H, CH$_2$CH$_2$Ph), 3.67 (q, J=6.1 Hz, 2H, CH$_2$CH$_2$NMe$_2$), 3.79 (s, 6H, 2×OCH$_3$), 4.22 (m, 2H, CH$_2$CH$_2$Ph), 6.72-6.75 (m, 3H, H-2', H-5' and H-6'), 7.41 (t, J=7.6 Hz, 1H, H-8), 7.64 (d, J=6.8 Hz, 1H, H-7), 7.77 (d, J=8.2 Hz, 1H, H-9), 8.51 (s, 1H, H-3), 9.15 (s, 1H, H-10), 10.83 (br t, J=5.3 Hz, 1H, CONH). $^{13}$C NMR (CDCl$_3$): δ 18.4 (ArCH$_3$), 34.9 (CH$_2$CH$_2$Ph), 37.5 (CH$_2$CH$_2$NMe$_2$), 45.4 [N(CH$_3$)$_2$], 51.2 (CH$_2$CH$_2$Ph), 55.8 (2×OCH$_3$), 58.7 (CH$_2$CH$_2$NMe$_2$), 109.5 (C-4), 111.4 (CH, Ar), 111.9 (CH, Ar), 119.3 (C-10a), 120.7 (CH, Ar), 125.7 (C-9a), 126.5 (CH, C-8), 127.2 (CH, C-9), 129.8 (C, Ar), 132.7 (CH, C-7), 135.8 (C-6), 139.7 (CH, C-10), 142.7 (CH, C-3), 147.8 (C, Ar), 148.0 (C-5a), 148.6 (C-4a), 149.0 (C, Ar), 162.2 (C-1), 164.3 (CONH).

Anal. Calc. for C$_{28}$H$_{32}$N$_4$O$_4$: C, 68.8; H, 6.6; N, 11.5. Found: C, 68.7; H, 6.9; N, 11.5.

N-[2-(Dimethylamino)ethyl]-6-methyl-2-(pyridin-2-yl)methyl-1-oxo-1,2-dihydrobenzo[b][1,6]-naphthyridine-4-carboxamide (20t)

From acid 18t, with a reflux time of 48 h and a recharge with an equal amount of CDI after 24 h, and obtained as a bright yellow solid (75%), mp 183-184° C., (from acetonitrile). $^1$H NMR (CDCl$_3$): δ 2.25 [s, 6H, N(CH$_3$)$_2$], 2.57 (t, J=6.4 Hz, 2H, CH$_2$CH$_2$NMe$_2$), 2.67 (s, 3H, ArCH$_3$), 3.66 (q, J=6.1 Hz, CH$_2$, CH$_2$CH$_2$NMe$_2$), 5.30 (s, 2H, CH$_2$Pyr), 7.10 (dd, J=7.0, 5.2 Hz, 1H, H-5'), 7.26-7.33 (m, 2H, H-3', H-8), 7.52-7.59 (m, 2H, H-4', H-7), 7.64 (d, J=8.2 Hz, 1H, H-9), 8.46 (d, J=4.4 Hz, 1H, H-6'), 8.66 (s, 1H, H-3), 9.02 (s, 1H, H-10), 10.79 (br t, J=5.1 Hz, 1H, CONH). $^{13}$C NMR (CDCl$_3$): δ 18.3 (ArCH$_3$), 37.3 (CH$_2$CH$_2$NMe$_2$), 45.2 [N(CH$_3$)$_2$], 53.7 (CH$_2$Pyr), 58.6 (CH$_2$CH$_2$NMe$_2$), 109.6 (C-4), 119.1 (C-10a), 122.1 (CH, C-3'), 122.7 (CH, C-5'), 125.5 (C-9a), 126.4 (CH, C-8), 127.0 (CH, C-9), 132.6 (CH, C-7), 135.6 (C-6), 136.7 (CH, C-4'), 139.6 (CH, C-10), 143.4 (CH, C-3), 147.7 (C-5a), 148.5 (C-4a), 149.6 (CH, C-6'), 155.0 (C-2'), 162.2 (C-1), 164.3 (CONH).

Anal. Calc. for C$_{24}$H$_{25}$N$_5$O$_2$: C, 69.4; H, 6.1; N, 16.9. Found: C, 69.1; H, 6.2; N, 16.8.

N-[2-(Dimethylamino)ethyl]-6-methyl-1-oxo-2-[3-(2-oxopyrrolidin-1-yl)propyl]-1,2-dihydrobenzo[b][1,6]-naphthyridine-4-carboxamide (20u)

From acid 18u with a reflux time of 24 h, and obtained as a yellow solid (89%), mp 170-171° C., (from acetonitrile). $^1$H NMR (CDCl$_3$): δ 1.96-2.06 (m, 4H), 2.25 [s, 6H, N(CH$_3$)$_2$], 2.35 (t, J=8.1 Hz, 2H), 2.58 (t, J=6.5 Hz, 2H), 2.75 (s, 3H, ArCH$_3$), 3.38 (m, 4H), 3.66 (q, J=5.9 Hz, 2H), 4.02 (m, 2H), 7.41 (dd, J=7.3, 7.9 Hz, 1H, H-8), 7.64 (d, J=6.9 Hz, 1H, H-7), 7.76 (d, J=8.1 Hz, 1H, H-9), 8.52 (s, 1H, H-3), 9.13 (s, 1H, H-10), 10.85 (br t, J=3.5 Hz, 1H, CONH). $^{13}$C NMR (CDCl$_3$): δ 17.6 (CH$_2$), 18.0 (ArCH$_3$), 26.6 (CH$_2$), 30.5 (CH$_2$), 37.2 (CH$_2$), 39.5 (CH$_2$), 45.0 [N(CH$_3$)$_2$], 46.6 (CH$_2$), 47.1 (CH$_2$), 58.3 (CH$_2$), 109.3 (C-4), 118.8 (C-10a), 125.3 (C-9a), 126.2 (CH, C-8), 126.8 (CH, C-9), 132.8 (CH, C-7), 135.4 (C-6), 139.2 (CH, C-10), 142.2 (CH, C-3), 147.6 (C-5a), 148.1 (C-4a), 161.8 (C-1), 163.9 (CONH), 174.8 (C-2').

Anal. Calc. for C$_{25}$H$_{31}$N$_5$O$_3$: C, 66.8; H, 7.0; N, 15.6. Found: C, 66.3; H, 7.1; N, 15.7.

N-[2-(Dimethylamino)ethyl]-7-methoxy-2-methyl-1-oxo-1,2-dihydro-benzo[b][1,6]naphthyridine-4-carboxamide (20w)

From acid 18w, with a reflux time of 96 h and a recharge with an equal amount of CDI after 48 h, and obtained as a yellow solid (80%), mp 213-215° C. (from acetonitrile). $^1$H NMR (CDCl$_3$): δ 2.50 [s, 6H, N(CH$_3$)$_2$], 2.78 (t, J=6.0 Hz, 2H, CH$_2$CH$_2$NMe$_2$), 3.67 (s, 3H, NCH$_3$), 3.77 (q, J=5.8 Hz, 2H, CH$_2$CH$_2$NMe$_2$), 4.02 (s, 3H, ArOCH$_3$), 7.22 (dd, J=9.1, 2.2 Hz, 1H, H-8), 7.43 (d, J=2.2 Hz, 1H, H-6), 7.85 (d, J=9.1 Hz, 1H, H-9), 8.53 (s, 1H, H-3), 9.14 (s, 1H, H-10), 11.36 (br s, 1H, CONH). $^{13}$C NMR (CDCl$_3$): δ 36.8 (CH$_2$CH$_2$NMe$_2$ and NCH$_3$), 45.0 [N(CH$_3$)$_2$], 55.6 (ArOCH$_3$), 57.7 (CH$_2$CH$_2$NMe$_2$), 105.3 (CH, C-6), 108.8 (C-4), 117.3 (C-10a), 120.9 (CH, C-8), 121.4 (C-9a), 130.0 (CH, C-9), 138.3 (CH, C-10), 143.1 (CH, C-3), 149.7 (C-4a), 150.9 (C-5a), 162.5 (C-1), 163.4 (C-7), 164.4 (CONH).

Anal. Calc. for C$_{19}$H$_{22}$N$_4$O$_3$C, 64.4; H, 6.3; N, 15.8. Found: C, 64.4; H, 6.5; N, 15.6.

N-[2-(Dimethylamino)ethyl]-2-[((2-(dimethylamino)ethyl)amino)carbonyloxy]ethyl-6-methyl-1-oxo-1,2-dihydrobenzo[b][1,6]naphthyridine-4-carboxamide (21a)

From acid 18h, with a reflux time of 48 h, and obtained as a yellow solid (63%), mp 75-76° C. (from toluene×3). $^1$H NMR (CDCl$_3$): δ 2.17 [s, 6H, N(CH$_3$)$_2$], 2.28 [s, 6H, N(CH$_3$)$_2$], 2.34 (t, J=6.0 Hz, 2H, CH$_2$CH$_2$NMe$_2$), 2.60 (t, J=6.5 Hz, 2H, CH$_2$CH$_2$NMe$_2$), 2.81 (s, 3H, ArCH$_3$), 3.19 (q, J=5.8 Hz, 2H, CH$_2$CH$_2$NMe$_2$), 3.69 (q, J=6.2 Hz, 2H, CH$_2$CH$_2$NMe$_2$), 4.32 (m, 2H, CH$_2$CH$_2$OCO), 4.41 (m, 2H, CH$_2$CH$_2$OCO), 5.82 (br s, 1H, CONH), 7.47 (t, J=7.6 Hz, 1H, H-8), 7.70 (d, J=6.8 Hz, 1H, H-7), 7.83 (d, J=8.1 Hz, 1H, H-9), 8.58 (s, 1H, H-3), 9.23 (s, 1H, H-10), 10.99 (br s, 1H, 4-position CONH). $^{13}$C NMR (CDCl$_3$): δ 18.2 (ArCH$_3$), 37.3 (CH$_2$CH$_2$NMe$_2$), 38.1 (CH$_2$CH$_2$NMe$_2$), 44.8 [N(CH$_3$)$_2$]$_1$, 45.1 [N(CH$_3$)$_2$], 48.8 (CH$_2$CH$_2$OCO), 58.0 (CH$_2$CH$_2$NMe$_2$), 58.5 (CH$_2$CH$_2$NMe$_2$), 61.9 (CH$_2$CH$_2$OCO), 109.0 (C-4), 119.0 (C-10a), 125.6 (C-9a), 126.3 (CH, C-8), 127.0 (CH, C-9), 132.6 (CH, C-7), 135.5 (C-6), 139.7 (CH, C-10), 143.4 (CH, C-3), 147.9 (C-5a), 148.4 (C-4a), 155.6 (CONH), 162.1 (C-1), 164.4 (CONH). HRMS (EI): Calc. for C$_{25}$H$_{34}$N$_6$O$_4$ [M+]: 482.2643. Found: 482.2626.

N-[2-(Dimethylamino)ethyl]-2-[N-(((2-(dimethylamino)ethyl)amino)carbonyl)-1H-indol-3-yl]ethyl-6-methyl-1-oxo-1,2-dihydrobenzo[b][1,6]naphthyridine-4-carboxamide (21b)

From acid 18v with a reflux time of 48 h and a recharge with an equal amount of CDI after 24 h, and obtained as a yellow solid (62%), mp 182-185° C., (from acetonitrile). $^1$H NMR (CDCl$_3$): δ2.27 [s, 12H, 2×N(CH$_3$)$_2$], 2.52-2.61 (m, 4H, 2×CH$_2$CH$_2$NMe$_2$), 2.77 (s, 3H, ArCH$_3$), 3.18 (t, J=7.7 Hz, 2H, CH$_2$CH$_2$Indole), 3.50 (q, J=5.4 Hz, 2H, 1'-CH$_2$CH$_2$NMe$_2$), 3.68 (q, J=6.0 Hz, 2H, 4-CH$_2$CH$_2$NMe$_2$), 4.32 (t, J=7.7 Hz, 2H, CH$_2$CH$_2$Indole), 6.60 (br t, J=4.1 Hz, 1H, 1'-CONH), 7.18 (t, J=7.4 Hz, 1H, H-5'), 7.27 (t, J=7.8 Hz, 1H, H-6'), 7.39-7.44 (m, 2H, H-2', H-8), 7.65 (m, 2H, H-4', H-7), 7.77 (d, J=8.2 Hz, 1H, H-9), 8.09 (d, J=8.2 Hz, 1H, H-7'), 8.55 (s, 1H, H-3), 9.17 (s, 1H, H-10), 10.87 (br t, J=5.2 Hz, 1H, 4-CONH). $^{13}$C NMR (CDCl$_3$): δ 18.4 (ArCH$_3$), 24.8 (CH$_2$CH$_2$Indole), 37.6 (4-CH$_2$CH$_2$NMe$_2$), 37.9 (1'-CH$_2$CH$_2$NMe$_2$), 45.0 [N(CH$_3$)$_2$], 45.4 [N(CH$_3$)$_2$], 49.7 (CH$_2$CH$_2$Indole), 57.7 (1'-CH$_2$CH$_2$NMe$_2$), 58.7 (4-CH$_2$CH$_2$NMe$_2$), 109.5 (C-4), 114.4 (CH, C-7'), 115.7 (1'-CONH), 118.8 (CH, C-4'), 119.3 (C-10a), 121.98 (CH, C-2'), 122.03 (CH, C-5'), 124.4 (CH, C-6'), 125.8 (C-9a), 126.5 (CH, C-8), 127.2 (CH, C-9), 129.5 (C, C-3a'), 132.8 (CH, C-7), 135.6 (C-7a'), 135.8 (C-6), 139.7 (CH, C-10), 142.7 (CH, C-3), 148.0 (C-5a), 148.5 (C-4a), 152.0 (C-3'), 162.2 (C-1), 164.4 (4-CONH).

Anal. Calc. for C$_{33}$H$_{39}$N$_7$O$_3$.0.5H$_2$O: C, 67.1; H, 6.8; N, 16.6. Found: C, 67.2; H, 6.7; N, 16.6.

Example 7

Preparation of N-[2-(Dimethylamino)ethyl]-2-hydroxyethyl-6-methyl-1-oxo-1,2-dihydrobenzo[b][1,6]-naphthyridine-4-carboxamide (20h).

This is an example of hydrolytic modification of a 2-substituent within a 4-carboxamide according to Scheme 2e.

To the carbamate 21a (0.55 g, 1.49 mmol) in ethanol (25 mL) was added 10% sodium hydroxide (20 mL), and the whole was heated under reflux for 1 h, then cooled on ice, adjusted to pH ~8 with concentrated hydrochloric acid, and evaporated to dryness at reduced pressure. The residual solid was boiled in acetonitrile, the mixture was filtered while hot, and the filtrate was taken to dryness at reduced pressure to give an orange solid (0.26 g). This solid was dissolved in a little warm ethanol and added to a bed of silica. This was eluted with a little ethanol, then with ethanol/triethylamine (25:1). The ethanol/triethylamine eluate was taken to dryness at reduced pressure. The residual solid (0.17 g) was dissolved in a little chloroform, filtered through a bed of basic alumina, washed with chloroform, and then eluted with methanol. The methanol eluate was evaporated to dryness under reduced pressure to give a yellow solid (0.12 g) which was recrystallized twice from dichloromethane to give the amide 20h as a yellow solid (0.10 g, 24%), mp 174-180° C. $^1$H NMR (CDCl$_3$): δ 2.27 [s, 6H, N(CH$_3$)$_2$], 2.43 (s, 3H, ArCH$_3$), 2.54 (t, J=6.4 Hz, 2H, CH$_2$CH$_2$NMe$_2$), 3.55 (q, J=6.0 Hz, 2H, CH$_2$CH$_2$NMe$_2$), 4.05 (m, 2H, CH$_2$CH$_2$OH), 4.20 (m, 2H, CH$_2$CH$_2$OH), 7.34 (t, J=7.5 Hz, 1H, H-8), 7.50 (d, J=6.7 Hz, 1H, H-7), 7.63 (d, J=8.1 Hz, 1H, H-9), 8.56 (s, 1H, H-3), 8.96 (s, 1H, H-10), 10.67 (br t, J=5.0 Hz, 1H, CONH). $^{13}$C NMR (CDCl$_3$): δ 17.9 (ArCH$_3$), 37.0 (CH$_2$CH$_2$NMe$_2$), 45.0 [N(CH$_3$)$_2$], 52.3 (CH$_2$CH$_2$OH), 58.1 (CH$_2$CH$_2$NMe$_2$), 60.2 (CH$_2$CH$_2$OH), 108.2 (C-4), 118.7 (C-10a), 125.1 (C-9a), 126.1 (CH, C-8), 126.8 (CH, C-9), 132.3 (CH, C-7), 135.3 (C-6), 139.0 (CH, C-10), 143.9 (CH, C-3), 147.3 (C-5a), 147.9 (C-4a), 162.4 (C-1), 164.3 (CONH). HRMS (LSI): Calc. for C$_{20}$H$_{25}$N$_4$O$_3$ [(M+H)+]: 369.1928. Found: 369.1940.

The filtrate from the chloroform washings was evaporated to dryness under reduced pressure to give 2-(2-(dimethylamino)ethyl)-4-[(2-(dimethylamino)ethylamino)methylene]-6-methyl-4H-benzo[b][1,6]naphthyridine-1,3-dione (22) as a yellow solid (0.04 g, 9%), mp 202-206° C. $^1$H NMR (CDCl$_3$): δ 2.28 [s, 6H, N(CH$_3$)$_2$], 2.34 [s, 6H, N(CH$_3$)$_2$], 2.58-2.72 (m, 4H, 2×CH$_2$CH$_2$NMe$_2$), 2.85 (s, 3H, ArCH$_3$), 3.66 (q, J=6.0 Hz, 2H, CH$_2$CH$_2$NMe$_2$), 4.26 (t, J=7.2 Hz, 2H, CH$_2$CH$_2$NMe$_2$), 7.34 (t, J=7.6 Hz, 1H, H-8), 7.60 (d, J=7.0 Hz, 1H, H-7), 7.72 (d, J=8.0 Hz, 1H, H-9), 8.44 (d, J=13.6 Hz, 1H, =CH), 8.95 (s, 1H, H-10), 11.76 (br m, 1H, NH). $^{13}$C NMR (CDCl$_3$): δ 18.3 (ArCH$_3$), 37.6 (CH$_2$CH$_2$NMe$_2$), 45.1 [N(CH$_3$)$_2$], 45.4 [N(CH$_3$)$_2$], 48.2 (CH$_2$CH$_2$NMe$_2$), 56.8 (CH$_2$CH$_2$NMe$_2$), 59.1 (CH$_2$CH$_2$NMe$_2$), 94.2 (C), 116.5 (C), 124.3 (C-9a), 124.5 (CH, C-8), 127.2 (CH, C-9), 131.9 (CH, C-7), 134.0 (C-6), 138.8 (CH, C-10), 147.8 (C-5a), 152.0 (C-4a), 155.8 (CH, =CH), 163.7 (C-1), 165.4 (C-3). ESMS: m/z 396.2 (M+1), 198.7 [(M+2)/2].

The following modification was carried out in a similar manner (Scheme 2f):

N-[2-(Dimethylamino)ethyl]-2-[2-(1H-Indol-3-yl)ethyl]-6-methyl-1-oxo-1,2-dihydrobenzo[b][1,6]naphthyridine-4-carboxamide (20v)

To a hot solution of the bisamide 21b (0.58 g, 1.00 mmol) in ethanol (10 mL) was added 10% sodium hydroxide (10 mL), and the whole was heated at reflux for 40 min. The reaction mixture was then evaporated to dryness under reduced pressure, water was added and the solid was filtered and washed with water to give 20v as a gold solid (0.42 g, 90%), mp 105-107° C. (from acetonitrile). $^1$H NMR (CDCl$_3$): δ 2.31 [s, 6H, N(CH$_3$)$_2$], 2.64 (t, J=6.4 Hz, 2H, CH$_2$CH$_2$NMe$_2$), 2.82 (s, 3H, ArCH$_3$), 3.21 (t, J=7.7 Hz, 2H, CH$_2$CH$_2$Indole), 3.73 (q, J=6.1 Hz, 2H, CH$_2$CH$_2$NMe$_2$), 4.30 (t, J=7.8 Hz, 2H, CH$_2$CH$_2$Indole), 6.99 (d, J=2.0 Hz, 1H, H-2'), 7.06-7.14 (m, 2H, H-5', H-6'), 7.30 (d, J=7.7 Hz, 1H, H-7'), 7.46 (t, J=7.6 Hz, 1H, H-8), 7.66-7.70 (m, 2H, H-4', H-7), 7.82 (d, J=8.2 Hz, 1H, H-9), 8.51 (s, 1H, H-3), 8.62 (s, 1H, H-1'), 9.24 (s, 1H, H-10), 10.98 (br t, J=5.3 Hz, 1H, CONH). $^{13}$C NMR (CDCl$_3$): δ 18.2 (ArCH$_3$), 24.8 (CH$_2$CH$_2$Indole), 37.2 (CH$_2$CH$_2$NMe$_2$), 45.0 [N(CH$_3$)$_2$], 50.2 (CH$_2$CH$_2$Indole), 58.4 (CH$_2$CH$_2$NMe$_2$), 109.0 (C), 110.9 (CH, C-7'), 111.1 (C), 118.2 (CH, C-4'), 119.2 (CH, C-5'), 121.7 (CH, C-6'), 122.0 (CH, C-2'), 125.6 (C-9a), 126.2 (CH, C-8), 126.8 (C-3a'), 127.0 (CH, C-9), 132.5 (CH, C-7), 135.5 (C-6), 136.0 (C-7a'), 139.5 (CH, C-3), 142.7 (CH, C-10), 147.8 (C-5a), 148.4 (C-4a), 162.1 (C-1), 164.4 (CONH). Indole C-3' was not observed.

HRMS (EI): Calc. for $C_{28}H_{29}N_5O_2$ [M$^+$]: 467.2323. Found: 467.2314.

Example 8

Anti-Tumour Activity In Vitro

The compounds identified in Table 1 were evaluated for growth inhibitory properties, measured as IC$_{50}$ values, against murine P388 leukemia cells, Lewis lung carcinoma cells (LLTC), and human Jurkat leukemia cells (JL$_C$), together with their amsacrine- and doxorubicin-resistant derivatives (JL$_A$ and JL$_D$ respectively), which were obtained and cultured as previously described (Finlay et al, 1990; 1994). Growth inhibition assays were performed by culturing cells in microculture plates (150 μl per well) as follows:

P388: 4.5×10$^3$ cells/well; 3 days

LLTC: 1×10$^3$ cells/well; 4 days

Jurkat lines: 3.75×10$^3$ cells/well; 4 days

Cell growth was determined by [$^3$H]-thymidine uptake (P388) (Marshall et al, 1992) or by the sulphorhodamine assay (Skehan et al, 1990). Independent assays were performed in duplicate, using doxorubicin, etoposide, camptothecin and DACA as reference compounds. The results are summarized in Table 2.

TABLE 2

Anti-Tumour Activity In Vitro of 1-oxo-1,2-dihydrobenzo[b][1,6]naphthyridine-4-carboxamides and prior art reference compounds

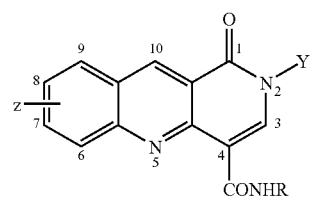

| Cpd | Y | Z | IC$_{50}$$^a$ (nM) P388$^c$ | LL$^d$ | JL$_c$$^s$ | IC$_{50\,ratio}$$^b$ A/C | D/C |
|---|---|---|---|---|---|---|---|
| 20b$^f$ | Me | H | 14 | | | | |
| 20c$^f$ | H | 6-Me | 11 | 10 | 26 | 1.9 | 2.6 |
| 20d$^f$ | Me | 6-Me | 2.1 | 1.7 | 6.7 | 5.6 | 7.9 |
| 20e$^f$ | Et | 6-Me | 3.7 | | | | |
| 20f$^f$ | Bu | 6-Me | 14 | 15 | 51 | 2.3 | 3.0 |
| 20g$^f$ | CH$_2$CF$_3$ | 6-Me | 61 | | | | |
| 20h$^f$ | (CH$_2$)$_2$OH | 6-Me | 4.8 | | | | |
| 20i$^f$ | CH$_2$CO$_2$Et | 6-Me | 12 | | | | |
| 20j$^f$ | (CH$_2$)$_3$CO$_2$Et | 6-Me | 10 | | | | |
| 20k$^f$ | (CH$_2$)$_2$NMe$_2$ | 6-Me | 6.8 | 3.7 | 8.5 | 0.7 | 0.9 |
| 20l$^f$ | (CH$_2$)$_2$NMe$_2$ | H | 54 | 50 | 123 | 0.8 | 1.1 |
| 20m$^f$ | CH(Me)Ph-(s) | 6-Me | 590 | 161 | 1070 | 0.8 | 1.1 |
| 20n$^f$ | Ph | 6-Me | 12 | | | | |
| 20o$^f$ | C$_6$H$_4$F-4 | 6-Me | 10 | | | | |
| 20p$^f$ | C$_6$H$_4$B(OH)$_2$-4 | 6-Me | 7.9 | | | | |
| 20q$^f$ | C$_6$H$_3$[3,4-(MeO)$_2$] | 6-Me | 12 | 4.4 | 9.4 | 1.3 | 1.5 |
| 20r$^f$ | CH$_2$C$_6$H$_3$[3,4-(MeO)$_2$] | 6-Me | 160 | | | | |
| 20s$^f$ | (CH$_2$)$_2$C$_6$H$_3$[3,4-(MeO)$_2$] | 6-Me | 810 | | | | |
| 20t$^f$ | CH$_2$(2-pyridinyl) | 6-Me | 13 | | | | |
| 20u$^f$ | 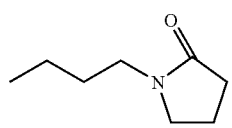 | 6-Me | 50 | | | | |

TABLE 2-continued

Anti-Tumour Activity In Vitro of 1-oxo-1,2-dihydrobenzo[b][1,6]naphthyridine-4-carboxamides and prior art reference compounds

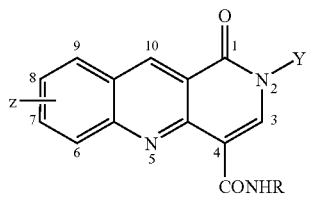

| | | | IC$_{50}$$^a$ (nM) | | | IC$_{50\,ratio}$$^b$ | |
|---|---|---|---|---|---|---|---|
| Cpd | Y | Z | P388$^c$ | LL$^d$ | JL$_c$$^s$ | A/C | D/C |
| 20v$^f$ | (indole-CH$_2$CH$_2$-) | 6-Me | 210 | | | | |
| 20w$^f$ | Me | 7-MeO | 36 | | | | |
| 20x$^f$ | Me | 6-Cl-7-MeO | 60 | | | | |
| 20y$^f$ | Me | 6-aza | 19 | | | | |
| 20z$^f$ | Me | 10-aza | 1000 | | | | |
| 21a$^f$ | (CH$_2$)$_2$OCONH(CH$_2$)$_2$NMe$_2$ | 6-Me | <125 | | | | |
| 21b$^f$ | (indole-N-CONH(CH$_2$)$_2$NMe$_2$, (CH$_2$)$_2$-) | 6-Me | 140 | | | | |
| 20aa$^{f,g}$ | (CH$_2$)$_2$NMe(CH$_2$)$_3$NMe(CH$_2$)$_2$ | 6-Me | 22 | 4.7 | 1.0 | 0.3 | 0.4 |
| 20bb$^h$ | Me | 6-Me | 17000 | | | | |
| 20cc$^i$ | Me | 6-Me | 5 | | | | |
| | doxorubicin | | 15 | 22 | 9.6 | 4.4 | 12.7 |
| | etoposide | | 25 | 180 | 160 | 13.3 | 90.3 |
| | camptothecin | | 13 | 33 | 5.6 | 2.0 | 1.4 |
| | 2 (DACA) | | 71 | 190 | 580 | 1.9 | 2.3 |

Footnotes
$^a$IC$_{50}$; concentration of drug to reduce cell number to 50% of control cultures.
$^b$IC$_{50}$ values for the Jurkat lines JL$_A$ and JL$_D$, respectively, relative to JL$_C$-see text
$^c$Murine P388 leukemia.
$^d$Murine Lewis lung carcinoma.
$^e$Human Jurkat leukemia.
$^f$R = CH$_2$CH$_2$NMe$_2$
$^g$A bis compound, an example of Formula II
$^h$R = (S)—CH(Me)CONMe$_2$
$^i$R = (S)—CH(Me)CH$_2$NMe$_2$ The JL$_A$ line is resistant to the DNA intercalator amsacrine and similar agents because of a reduced level of topo II enzyme. The JL$_D$ line is resistant to doxorubicin, primarily by virtue of altered levels of topo II, but probably also via additional mechanisms. The ratios of the IC$_{50}$ values of a drug in the parent line compared with one of the sublines (IC$_{50}$[JL$_A$]/IC$_{50}$[JL$_C$] and (IC$_{50}$[JL$_D$]/IC$_{50}$[JL$_C$]) therefore provide some indication of the mechanism of cytotoxicity. Classical topo II inhibitors such as amsacrine, doxorubicin and etoposide have large ratios (10-90 fold), whereas topo I inhibitors such as camptothecin and mixed topo I/II inhibitors such as DACA (4) have ratios of only about 2-fold. Values of these ratios of less than about 1.5-2 therefore suggest cytotoxicity by a non-topo II mediated mechanism.

Example 9

Anti-Tumour Activity In Vivo

Compound 20d was evaluated against murine colon 38 tumours implanted subcutaneously in C57BL/6 mice. This advanced colon 38 tumour model is fairly refractory to standard clinical topo II agents, as well as to anti-metabolites and alkylating agents. In vivo models using the colon 38 tumour model have been shown to be the best predictors for clinical utility to date (Goldin, A, 1980). It therefore represents a good test for in vivo activity.

Figure 3:
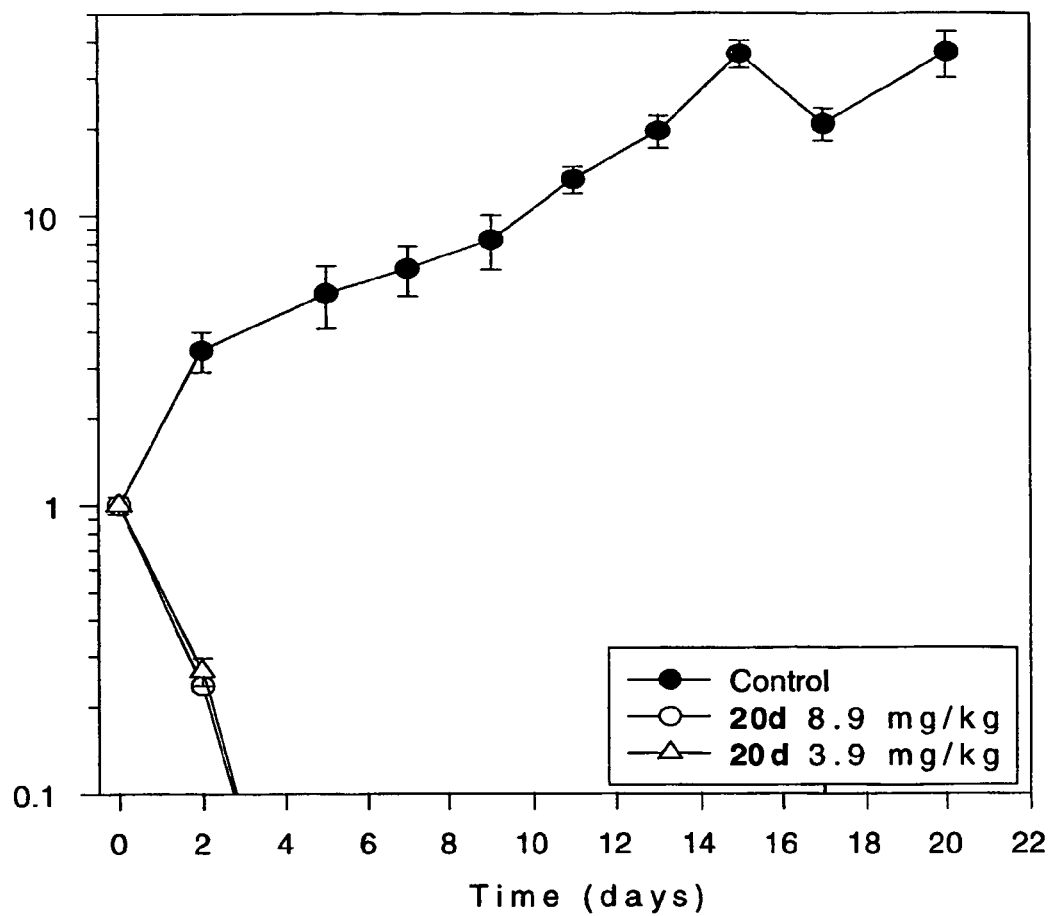
FIG. 3 is a graph showing a comparison between the growth of transplanted tumour in the colon 38 in control mice (●) and those receiving a single dose of 20d (8.9 mg/kg; ○) (3.9 mg/kg; Δ).

Colon 38 tumours were grown subcutaneously from 1 mm³ fragments implanted in one flank of C57/B1 mice (anaesthetised with pentobarbitone 90 mg/kg). When tumours reached a diameter of approximately 4 mm (7-8 days), mice were divided into control and drug treatment groups (5 mice/group), with similar average tumour volumes in each group. Drugs were administered as solutions of the hydrochloride salts in distilled water, and were injected in a volume of 0.01 mL/g body weight. Mice treated with the prior art compounds Doxorubicin, Daunorubicin, Amsacrine, Mitoxantrone, DACA, Etoposide or Irinotecan were used as positive controls. The mice were monitored closely, and tumour diameters were measured with callipers three times a week. Tumour volumes were calculated as $0.52xa^2xb$, where a and b are the minor and major tumour axes, and data plotted on a semilogarithmic plot as mean tumour volumes (±SEM) versus time after treatment. The results for 20d are shown in FIG. 3 and summarized for all compounds in Table 3. The growth delay was calculated as the time taken for tumours to reach a mean volume four-fold higher than their pre-treatment volume.

TABLE 3

In Vivo Activity of 1-Oxo-1,2-dihydrobenzo[b] [1,6]naphthyridine-4-carboxamides and Reference Compounds Against Subcutaneous Colon 38 Tumours in Mice

| Drug | Dose mg/kg/day | Schedule[a] | Growth delay days | Cures[b] |
|---|---|---|---|---|
| 20c | 30[c] | s.d. | 14 | 0/5 |
| 20d | 8.9[c] | s.d. | >20 | 4/4 |
| 20d | 5.9 | s.d. | >20 | 10/10 |
| 20d | 3.9 | s.d. | >20 | 4/4 |
| 20d | 2.6 | s.d. | 10 | 0/5 |
| 20f | 13.3[c] | s.d. | >20 | 5/5 |
| 20f | 5.9 | s.d. | 18 | 0/5 |
| 20k | 5.9 | s.d. | 14 | 0/5 |
| 20q | 3.9[c] | s.d. | >20 | 4/5 |
| 20q | 2.6 | s.d. | 16 | 0/5 |
| Doxorubicin | 2.6 | q4 d × 3 | 8 | 0/5 |
| Daunorubicin | 3.9 | q4 d × 3 | 0 | 0/5 |
| Amsacrine | 13.3 | q4 d × 3 | 2 | 0/5 |
| Mitoxantrone | 3.9 | q4 d × 3 | 2 | 0/5 |
| DACA | 200 | q7 d × 2 | 13 | 0/5 |
| Etoposide | 45 | q4 d × 3 | 1.5 | 0/5 |
| Irinotecan | 65 | q4 d × 3 | 7 | 0/5 |

[a] q2 d × 2 = every 2 days × 2; q4 d × 3 = every 4 days × 3; q7 d × 2 = every 7 days × 2; s.d. = single dose.
[b] Number of mice with no measurable tumour 20 days after commencement of treatment/total number of mice.
[c] Highest dose which did not produce evidence of toxicity.

It is evident from Table 3 that of the prior art compounds tested, only Doxorubicin, Irinotecan, and DACA resulted in a significant delay in growth of the Colon 38 tumour, and none resulted in long term survival. However, single doses of compound 20d resulted in a growth delay of at least 20 days at all but the lowest dosage level. In these cases, the mice treated were long term survivors, with no tumour present at 60 days after the end of treatment. Theoretically this is long enough for a single surviving cell to repopulate the tumour, so these mice would almost certainly have had normal life spans if held for a sufficiently long time.

Example 10

Anti-Tumour Activity In Vivo

Figure 4:
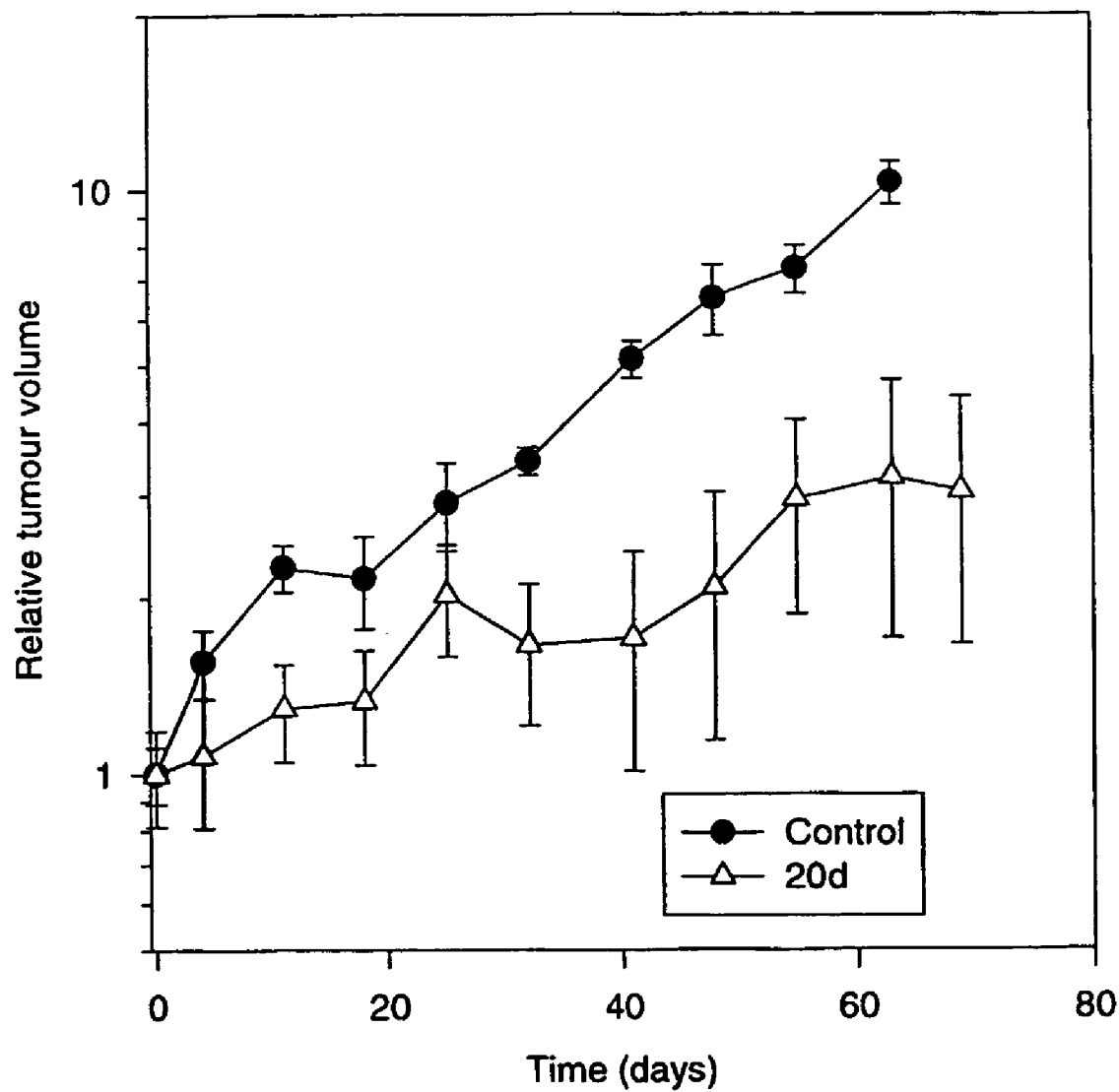
FIG. 4 is a graph showing a comparison between the growth of NZM4 melanoma cell line implanted subcutaneously in control mice (●) and those receiving 20d in two doses of 5.9 mg/kg, administered 7 days apart (Δ).

Compound 20d was evaluated against a human melanoma xenograft and demonstrated a tumour growth delay of 30 days when given in two doses of 5.9 mg/kg, administered 7 days apart. The NZM4 melanoma cell line (Marshall et al., 1994) was grown in culture and $1 \times 10^7$ cells were implanted subcutaneously in one flank of athymic (nude) mice. When tumours reached a diameter of approximately 6 mm (15 days), mice were divided into control and drug treatment groups (5 mice/group), with similar average tumour volumes in each group. Drugs were administered as solutions of the hydrochloride salts in distilled water and were injected in a volume of 0.01 mL/g body weight. The mice were monitored closely, and tumour diameters were measured with callipers twice per week. Tumour volumes were calculated as $0.52xa^2xb$, where a and b are the minor and major tumour axes, and data plotted on a semilogarithmic plot as mean tumour volumes (±SEM) versus time after treatment. The results for 20d are shown in FIG. 4. The growth delay was calculated as the time taken for tumours to reach a mean volume three-fold higher than their pre-treatment volume.

Discussion

The results show that the compounds of the present invention have cytotoxic activity against animal and human tumour cell lines, and are active against transplanted tumours in mice. Thus they have potential utility as anti-cancer drugs.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

References cited herein are listed on the following pages, and are incorporated herein by this reference.

REFERENCES

Ames, D. E. and Dodds, W. D. *J. Chem. Soc. Perkin Trans. 1*, 1972, 705.
Antonini, I.; Cola, D.; Polucci, P.; Bontemps-Gracz, M.; Borowski, E.; Martelli, S. *J. Med. Chem.* 1995, 38, 3282.
Asbury, R.; Blessing, J. A.; Reid, G. C.; McGuire. W. P. *Am. J. Clin. Oncol.* 1998, 21, 406.
Asherson, J. L. and Young, D. W. *J. Chem. Soc., Chem. Comm.*, 1977, 916.
Atwell, G. J.; Rewcastle, G. W.; Baguley, B. C. and Denny, W. A. *J. Med. Chem.* 1987, 30, 664.
Baguley, B. C.; Zhuang, L. and Marshall, E. M. *Cancer Chemother. Pharmacol.* 1995, 36, 244.
Cholody, W. M.; Hernandez, L.; Hassner, L.; Scudiero, D. A.; Djurickovic, D. B. and Michejda, C. J. *J. Med. Chem.* 1995, 38, 3043.
Cholody, W. M.; Horowska, B.; Paradziej-Lukowicz, J.; Martelli, S.; Konopa, J. *J. Med. Chem.,* 1996, 39, 1028.
Deady, L. W.; Kaye, A. J.; Finlay, G. J.; Baguley, B. C. and Denny, W. A. *J. Med. Chem.,* 1997, 40, 2040.
Deady, L. W.; Desneves, J.; Kaye, A. J.; Finlay, G. J.; Baguley, B. C. and Denny, W. A. *Bioorg. Med. Chem.,* 2000, 8, 977.
Deady, L. W. and Rodemann, T. *J. Heterocycl. Chem.,* 2001, 38, 1185.

Denny, W. A. Proceedings of the 13th Annual Conference of the Royal Australian Chemical Institute Medicinal and Agricultural Division 1996, Abstract 5-1.

Diab, S. G.; Baker, S. D.; Joshi, A.; Burris, H. A.; Cobb, P. W.; Villalona-Calero, M. A.; Eckhardt, S. G.; Weiss, G. R.; Rodriguez, G. I.; Drengler, R.; Kraynak M.; Hammond, L.; Finizio, M.; Von Hoff, D. D.; Rowinsky, E. K. *Clin. Cancer Res.,* 1999, 5, 299.

Finlay, G. J.; Baguley, B. C.; Snow, K. and Judd, W. *J. Natl. Cancer Inst.* 1990, 82, 662.

Finlay, G. J.; Holdaway, K. M.; Baguley, B. C. *Oncol. Res.* 1994, 6, 33-37.

Gabriel, S. *Ber. Dtsch. Chem. Ges.,* 1885, 18, 2445, 3470.

Gamage, S. A.; Spicer, J. A.; Finlay, G. J.; Stewart, A. J.; Charlton, P.; Baguley, B. C. and Denny, W. A. *J. Med. Chem.,* 2001, 44, 1407.

Goldin, A.; Venditti, J. M; Progress report on the screening program at the division of cancer treatment, *NCI. Cancer Treat. Rev.* 1980, 7, 167-176.

Jhalani, V. K.; Ghalsasi, L. P.; Acharya, S. P. and Usgaonkar, R. N. *Indian J. Chem.,* 1989, 28B, 173.

Judson, I. R. *Semin. Oncol.,* 1992, 687.

Khattab, A. F. *Liebigs Ann.,* 1996, 393.

Koller, C. A.; Kantarjian, H. M.; Feldman, E. J.; O'Brien, S.; Rios, M. B.; Estey, E. and Keating, M. *Cancer,* 1999, 86, 2246.

Kubo, K.; Ukawa, K.; Kuzuna, S. and Nohara, A. *Chem. Pharm. Bull.* 1986; 34; 1108.

Leaf, A. N.; Neuberg, D.; Schwartz, E. L.; Wadler, S.; Ritch, P. S.; Dutcher, J. P.; Adams, G. L. *Inv. New Drugs,* 1997, 15, 165.

Marshall, E. S.; Finlay, G. J.; Matthews, J. H. L.; Shaw, J. H. F.; Nixon, J. and Baguley, B. C. *J. Natl. Cancer Inst.,* 1992, 84, 340.

Marshall, E. S.; Matthews, J. H. L.; Shaw, J. H. F.; Nixon, J.; Tumewu, P.; Finlay, G. J.; Holdaway, K. M.; Baguley, B. C. *Eur. J. Cancer* 1994, 30A, 1370.

McFadyen, W. D.; Grant, L-C and Denny, W. A. Proceedings of the 13th Annual Conference of the Royal Australian Chemical Institute Medicinal and Agricultural Division 1996, Abstract 5-5.

Meth-Cohn, O. *Sth. Afr. J. Chem.,* 1987, 40, 189.

Modi, A. R. and Usgaonkar, R. N. *Indian J. Chem.,* 1979, 18B, 304.

Riou, J-F.; Rossé, P.; Nguyen, C. H.; Larsen, A. K.; Bissery, M-C.; Grondard, L.; Saucier, J-M.; Bisagni, E. and Lavelle, F. *Cancer Res.,* 1993, 53, 5987.

Rivalle, C. and Bisagni, E. *J. Heterocycl. Chem.,* 1980, 17, 245.

Sami, S. M.; Dorr, R. T.; Alberts, D. S.; Solyom, A. M. and Remers, W. A. *J. Med. Chem.,* 1996, 39, 4978.

Skehan, P.; Storeng. R.; Scudiero, D.; Monks, A.; McMahon. J.; Vistica, D.; Warren, J. T.; Bokesch, H.; Kenney. S. and Boyd, M. R. *J. Natl. Cancer Inst.* 1990, 82, 1107.

Stefanska, B.; Dzieduszycka, M.; Martelli, S.; Tarasiuk, J.; Bontemps-Gracz, M. and Borowski, E. *J. Med. Chem.,* 1993, 36, 38.

Stewart, A. J.; Mistry, P.; Dangerfield, W.; Bootle, D.; Baker, M.; Kofler, B.; Okiji, S.; Baguley, B. C.; Denny, W. A. and Charlton, P. A. *Anticancer Drugs,* 2001, 12, 359.

Thompson, J.; Pratt, C. B.; Stewart, C. F.; Avery, L.; Bowman, L.; Zamboni, W. C. and Pappo, A. *Inv. New Drugs,* 1998, 16, 45.

Utsugi, T.; Aoyagi, K.; Furune, Y.; Sano, M.; Wierzba, K.; Okazaki, S.; Asao, T. and Yamada, Y. *Proc. Am. Assoc. Cancer Res.,* 1996, 37, 427 (abstr. 2915).

Vicker, N.; Burgess, L.; Chuckowree, I. S.; Dodd, R.; Folkes, A. J.; Hardick, D. J.; Nancox, D. C.; Miller, W.; Milton, J.; Sohal, S.; Wang, S. M.; Wren, S. P.; Charlton, P. A.; Dangerfield, W.; Liddle, C.; Mistry, P.; Stewart, A. J. and Denny, W. A. *J. Med. Chem.,* 2002, 45, 721.

Vijayalakshmi, S. and Rajendran, S. P. *Indian J. Chem.,* 1994, 33B, 159.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The claims defining the invention are as follows:

1. A compound of the formula I

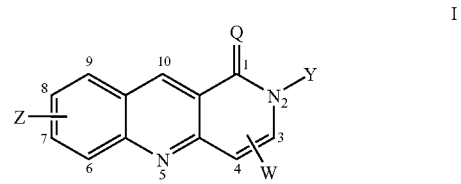

in which positional numbering, where mentioned, refers to the system illustrated above, and one or more Z are attached to a ring carbon or carbons at any of positions 6 to 10, and in which:

Q is O or S;

W is $C(=Q)NR-M-(CH_2)_m R^1$, in which

M is CHJ or G,

R is H or an optionally substituted $C_{1-4}$ alkyl group,

J is H or an optionally substituted $C_1$-$C_6$ alkyl group,

G is an optionally substituted fully saturated, or partially unsaturated, or aromatic, carbocycle or heterocycle, $R^1$ is $C(NR^2)NH_2$, $NHC(=NR^3)NH_2$ or $NR^4R^5$, in which each of $R^2$ and $R^3$ are independently H or an optionally substituted $C_{1-4}$ alkyl group, $R^4$ and $R^5$ are independently H or an optionally substituted $C_{1-4}$ alkyl group or $R^4$ and $R^5$ together with the nitrogen atom to which they are attached form an optionally substituted, saturated or unsaturated heterocyclic group, and m is an integer from 0 to 6;

Y is H, $C_{1-6}$ alkyl or $(CH_2)_n-X-(CH_2)_p U$, in which

X is $CH_2$, $C=O$, $CH=CH$, O, S, NR or G; and n and p are integers from 0 to 6, and U is H, $CF_3$, halo, $NR^4R^5$, $^+NRR^4R^5$, cyano, $C(=O)NR^4R^5$, $OR^4$, $CO_2R^5$, G, $NR^4G$ or OG; and Z is H, halo, OH, $CO_2H$, $CO_2R^4$, $SO_2R^4$, $NR^4R^5$, nitro, cyano, $C_{1-6}$ alkyl, $C_{1-6}$ haloalkyl, $C_{1-6}$ alkoxy, $C_{1-6}$ haloalkoxy, $C_{1-6}$ aminoalkyl, $C_{1-6}$ aminoalkoxy, or aza functionality replacing a ring CH functionality, or a carbon or carbon/nitrogen framework bridging the 6-7,7-8 or 8-9 positions so as to form an additional fused 5 to 6-membered carbocycle or heterocycle; or a pharmaceutically-acceptable salt thereof.

2. A compound according to claim 1, in which the optional substituents for R, $R^2$, $R^3$, $R^4$ and $R^5$ are one or more OH or $NH_2$ groups.

3. A compound according to claim 1, in which the optional substituents for J are one or more OH, OMe, $NH_2$, NHMe or $NMe_2$ groups.

4. A compound according to claim 1, in which the substituents for G are one or more halo, OH, $CO_2H$, $NR^4R^5$, NRSO$_2$R, SO$_2$NR$^4$R$^5$, nitro, cyano, C$_{1-6}$ alkyl, C$_{1-6}$ haloalkyl, C$_{1-6}$ alkoxy, C$_{1-6}$ haloalkoxy, C$_{1-6}$ aminoalkyl, C$_{1-6}$ aminoalkoxy or B (OR$^6$) (OR$^7$) in which R$^6$ and R$^7$ are independently hydrogen or an optionally substituted C$_{1-4}$ alkyl group or together with the O and B atoms to which they are attached form an optionally substituted, fully saturated, or partially unsaturated, heterocycle.

5. A compound according to claim 1, in which Q is O; W is COHN(CH$_2$)$_2$N(CH$_3$)CH$_2$ or CONCHN(CH$_3$)$_2$; Y is methyl, butyl or methoxy-substituted phenyl; and Z is H, Cl, methyl or methoxy.

6. A compound according to claim 1, which is N-[2-(dimethylamino)ethyl]-2,6-dimethyl-1-oxo-1,2-dihydrobenzo[b][1,6]naphthyridine-4-carboxamide or a pharmaceutically acceptable salt thereof.

7. A process for the preparation of a compound of formula I

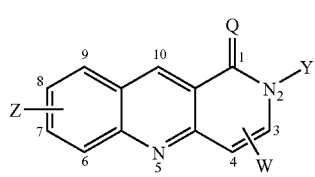

I in which positional numbering, where mentioned, refers to the system illustrated above, and one or more Z in formula I are attached to a ring carbon or carbons at any of positions 6 to 10, Q is O or S;
W is C(=Q)NR-M-(CH$_2$)$_M$R$^1$, in which
M is CHJ or G,
R is H or an optionally substituted C$_{1-4}$ alkyl group,
J is H or an optionally substituted C$_1$-C$_6$ alkyl group,
G is an optionally substituted fully saturated, or partially unsaturated, or aromatic, carbocycle or heterocycle,
R$^1$ is C(NR$^2$)NH$_2$, NHC(=NR$^3$)NH$_2$ or NR$^4$R$^5$, in which each of R$^2$ and R$^3$ are independently H or an optionally substituted C$_{1-4}$ alkyl group,
R$^4$ and R$^5$ are independently H or an optionally substituted C$_{1-4}$ alkyl group or R$^4$ and R$^5$ together with the nitrogen atom to which they are attached form an optionally substituted, saturated or unsaturated heterocyclic group, and
m is an integer from 0 to 6;
Y is H, C$_{1-6}$ alkyl or (CH$_2$)$_n$—X—(CH$_2$)$_p$U, in which
X is CH$_2$, C=O, CH=CH, O, S, NR or G; and
n and p are integers from 0 to 6, and
U is H, CF$_3$, halo, NR$^4$R$^5$, $^+$NRR$^4$R$^5$, cyano, C(=O)NR$^4$R$^5$, OR$^4$, CO$_2$R$^5$, G, NR$^4$G or OG; and
Z is H, halo, OH, CO$_2$H, CO$_2$R$^4$, SO$_2$R$^4$, NR$^4$R$^5$, nitro, cyano, C$_{1-6}$ alkyl, C$_{1-6}$ haloalkyl, C$_{1-6}$ alkoxy, C$_{1-6}$ haloalkoxy, C$_{1-6}$ aminoalkyl, C$_{1-6}$ aminoalkoxy, or aza functionality replacing a ring CH functionality, or a carbon or carbon/nitrogen framework bridging the 6-7, 7-8 or 8-9 positions so as to form an additional fused 5 to 6-membered carbocycle or heterocycle;
a pharmaceutically-acceptable salt thereof,
which comprises converting a compound of formula IV

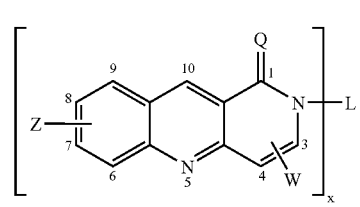

II

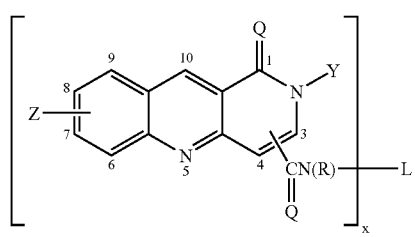

III in which one or more Z and one or more CO$_2$H groups are attached to a ring carbon or carbons at any of positions 6 to 10.

8. A process according to claim 7, in which the conversion step involves an intermediate step in which the compound of formula IV is converted into an imidazolide having the formula:

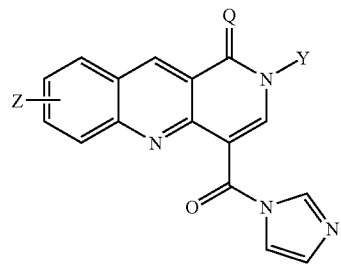

and then reacted with the appropriate amine to obtain the amide of formula I.

9. A process according to claim 7, in which the carboxylic acid of formula IV is converted into an acid halide, followed by reaction with an amine to obtain the amide of formula I.

10. A pharmaceutical or veterinary composition comprising the compound of claim 1 together with a pharmaceutically or veterinarily acceptable carrier.

* * * * *

UNITED STATES PATENT AND TRADEMARK OFFICE
CERTIFICATE OF CORRECTION

PATENT NO.        : 7,504,507 B2
APPLICATION NO.   : 10/514523
DATED             : March 17, 2009
INVENTOR(S)       : Baguley et al.

It is certified that error appears in the above-identified patent and that said Letters Patent is hereby corrected as shown below:

In claim 1, column 42, line 20, please delete the chemical structure, and substitute the following chemical structure:

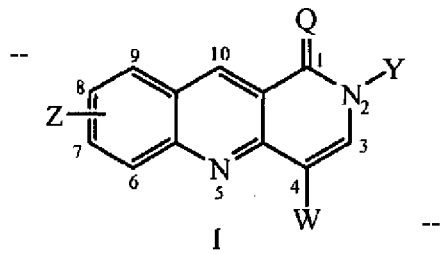

In claim 5, column 43, line 9, please delete "or $CONCHN(CH_3)_2$;" and substitute the following:

-- or $CONHCH (CH_3) CH_2N (CH_3)_2$; --

In claim 7, column 43, line 20, please delete the chemical structure, and substitute the following chemical structure:

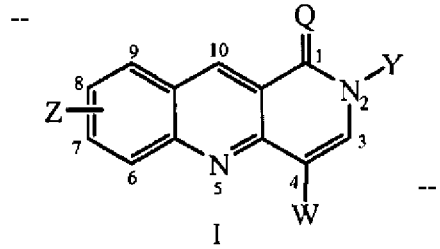

UNITED STATES PATENT AND TRADEMARK OFFICE
CERTIFICATE OF CORRECTION

PATENT NO. : 7,504,507 B2
APPLICATION NO. : 10/514523
DATED : March 17, 2009
INVENTOR(S) : Baguley et al.

It is certified that error appears in the above-identified patent and that said Letters Patent is hereby corrected as shown below:

In claim 7, column 44, lines 8-25, please delete the <u>two</u> chemical structures, and substitute the following chemical structure:

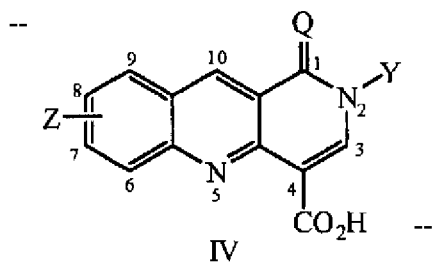

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,504,507 B2  Page 1 of 1
APPLICATION NO. : 10/514523
DATED : March 17, 2009
INVENTOR(S) : Baguley et al.

It is certified that error appears in the above-identified patent and that said Letters Patent is hereby corrected as shown below:

On the title page, item [73]:

"Assignee," please insert the following:

-- La Trobe University (NZ) --

Signed and Sealed this

Twenty-sixth Day of January, 2010

David J. Kappos
*Director of the United States Patent and Trademark Office*